US008187845B2

(12) United States Patent
Bailey et al.

(10) Patent No.: US 8,187,845 B2
(45) Date of Patent: *May 29, 2012

(54) ENHANCED PRODUCTION OF LIPIDS CONTAINING POLYENOIC FATTY ACID BY VERY HIGH DENSITY CULTURES OF EUKARYOTIC MICROBES IN FERMENTORS

(75) Inventors: Richard B. Bailey, Del Mar, CA (US); Don DiMasi, San Diego, CA (US); John M. Hansen, Chula Vista, CA (US); Peter J. Mirrasoul, San Diego, CA (US); Craig M. Ruecker, San Diego, CA (US); George T. Veeder, III, Casa Grande, AZ (US); Tatsuo Kaneko, San Diego, CA (US); William R. Barclay, Bouler, CO (US)

(73) Assignee: Martek Biosciences Corporation, Columbia, MD (US)

( * ) Notice: Subject to any disclaimer, the term of this patent is extended or adjusted under 35 U.S.C. 154(b) by 984 days.

This patent is subject to a terminal disclaimer.

(21) Appl. No.: 11/745,531

(22) Filed: May 8, 2007

(65) Prior Publication Data

US 2008/0032387 A1 Feb. 7, 2008

Related U.S. Application Data

(63) Continuation of application No. 11/352,421, filed on Feb. 10, 2006, now Pat. No. 7,579,174, and a continuation of application No. 10/371,394, filed on Feb. 21, 2003, now abandoned, which is a continuation of application No. 09/771,352, filed on Jan. 26, 2001, now Pat. No. 6,607,900.

(60) Provisional application No. 60/178,588, filed on Jan. 28, 2000.

(51) Int. Cl.
 C12P 7/64 (2006.01)
 C12N 1/14 (2006.01)
(52) U.S. Cl. ............... 435/134; 435/254.1; 435/911
(58) Field of Classification Search ............ None
 See application file for complete search history.

(56) References Cited

U.S. PATENT DOCUMENTS

| | | |
|---|---|---|
| 2,879,162 A | 3/1959 | Baldini et al. |
| 2,890,989 A | 6/1959 | Anderson |
| 3,108,402 A | 10/1963 | Kathrein |
| 3,142,135 A | 7/1964 | Kathrein |
| 3,282,794 A | 11/1966 | Okumura et al. |
| 3,296,079 A | 1/1967 | Griffin et al. |
| 3,316,674 A | 5/1967 | Shirota |
| 3,444,647 A | 5/1969 | Takahashi |
| 3,617,299 A | 11/1971 | Mattoon et al. |
| 3,647,482 A | 3/1972 | Yueh |
| 3,661,663 A | 5/1972 | Shannon |
| 3,667,969 A | 6/1972 | Kracauer |
| 3,761,588 A | 9/1973 | Tsuruoka et al. |
| 3,879,890 A | 4/1975 | Chen et al. |
| 3,882,635 A | 5/1975 | Yamanaka et al. |
| 3,908,026 A | 9/1975 | Neely et al. |
| 3,908,028 A | 9/1975 | Neely et al. |
| 3,924,017 A | 12/1975 | Lee et al. |
| 4,162,324 A | 7/1979 | Cassidy et al. |
| 4,229,544 A | 10/1980 | Haynes et al. |
| 4,232,122 A | 11/1980 | Zilliken |
| 4,281,064 A | 7/1981 | Suzuki et al. |
| 4,292,331 A | 9/1981 | Ostre |
| 4,304,794 A | 12/1981 | Dwivedi et al. |
| 4,341,038 A | 7/1982 | Bloch et al. |
| 4,367,178 A | 1/1983 | Heigel et al. |
| 4,383,038 A | 5/1983 | Leavitt |
| 4,405,649 A | 9/1983 | Jeffreys et al. |
| 4,425,396 A | 1/1984 | Hartman |
| 4,426,396 A | 1/1984 | Young |
| 4,474,773 A | 10/1984 | Shinitzky et al. |
| 4,554,390 A | 11/1985 | Curtain et al. |
| 4,588,600 A | 5/1986 | Suderman |
| 4,615,839 A | 10/1986 | Seto et al. |
| 4,634,533 A | 1/1987 | Somerville et al. |
| 4,670,285 A | 6/1987 | Clandinin et al. |
| 4,749,522 A | 6/1988 | Kamarei |
| 4,758,438 A | 7/1988 | Stroz et al. |
| 4,764,392 A | 8/1988 | Yasufuku et al. |
| 4,783,408 A | 11/1988 | Suzuki et al. |
| 4,792,418 A | 12/1988 | Rubin et al. |
| 4,822,500 A | 4/1989 | Dobson, Jr. et al. |
| 4,871,551 A | 10/1989 | Spencer |
| 4,874,629 A | 10/1989 | Chang et al. |

(Continued)

FOREIGN PATENT DOCUMENTS

AU 657259 B2 3/1995

(Continued)

OTHER PUBLICATIONS

Addy et al. "Dissolved Oxygen and Temperature" Natural Resources Facts, Fact Sheet 96-3, Mar. 1997, 4 pages. Barclay, "Production of Docosahexaenoic Acid from Microalgae and Its Benefits for Use in Animal Feeds", Simopoulos Ap (ed): The Return of w3 Fatty Acids Into the Food Supply. I. Land-Based Animal Food Products and Their Health Effects. World Rev Nutr Diet. Basel, Karger, 1998, vol. 83, pp. 61-76.
Beach et al. Biochimica and Biophysica Acta. 1973. 316:56-65.
Biology and Water Pollution Control, W.B. Saunders Company, Philadelphia, 1971, pp. 51-54.
Calvalier-Smith et al., Thraustochytrids are chromists, not Fungi: 18s rRNA signatures of Heterokonta, Phil. Trans. Royal Soc. London Bio Sciences, vol. 346, pp. 387-397, 1994.
Gaudy et al., in Microbiology for Environmental Scientists and Engineers, McGraw-Hill Book Company, New York, 1980, pp. 217-222.
Goldstein; "Zoosporic Marine Fungi (Thraustochytriaceae and Dermosystidiaceae"; Brooklyn College; Dept. of Biology; 1973, pp. 13-26.

(Continued)

Primary Examiner — Vera Afremova
(74) Attorney, Agent, or Firm — Sterne, Kessler, Goldstein & Fox PLLC

(57) ABSTRACT

The present invention provides a process for growing eukaryotic microorganisms which are capable of producing lipids, in particular lipids containing polyenoic fatty acids. The present invention also provides a process for producing eukaryotic microbial lipids.

6 Claims, 1 Drawing Sheet

U.S. PATENT DOCUMENTS

| | | | |
|---|---|---|---|
| 4,911,944 A | 3/1990 | Holub |
| 4,913,915 A | 4/1990 | Tanaka |
| 4,918,104 A | 4/1990 | Weiss et al. |
| 4,938,984 A | 7/1990 | Traitler et al. |
| 4,957,748 A | 9/1990 | Winowiski |
| 5,012,761 A | 5/1991 | Oh |
| 5,023,091 A | 6/1991 | Winowiski |
| 5,064,665 A | 11/1991 | Klopfenstein et al. |
| 5,130,242 A | 7/1992 | Barclay |
| 5,133,963 A | 7/1992 | Ise |
| 5,234,699 A | 8/1993 | Yeo |
| 5,244,921 A | 9/1993 | Kyle et al. |
| 5,272,085 A | 12/1993 | Young et al. |
| 5,338,673 A | 8/1994 | Thepenier et al. |
| 5,340,594 A | 8/1994 | Barclay |
| 5,340,742 A | 8/1994 | Barclay |
| 5,374,657 A | 12/1994 | Kyle |
| 5,407,957 A | 4/1995 | Kyle et al. |
| 5,415,879 A | 5/1995 | Oh |
| 5,492,828 A | 2/1996 | Premuzic et al. |
| 5,492,938 A | 2/1996 | Kyle et al. |
| 5,518,918 A | 5/1996 | Barclay |
| 5,547,699 A | 8/1996 | Iizuka et al. |
| 5,656,319 A | 8/1997 | Barclay |
| 5,658,767 A | 8/1997 | Kyle |
| 5,688,500 A | 11/1997 | Barclay |
| 5,698,244 A | 12/1997 | Barclay |
| 5,908,622 A | 6/1999 | Barclay |
| 5,958,426 A | 9/1999 | Moreau et al. |
| 5,985,348 A | 11/1999 | Barclay |
| 6,054,147 A | 4/2000 | Barclay |
| 6,103,225 A | 8/2000 | Barclay |
| 6,140,486 A | 10/2000 | Facciotti et al. |
| 6,177,108 B1 | 1/2001 | Barclay |
| 6,255,505 B1 | 7/2001 | Bijl et al. |
| 6,403,345 B1 | 6/2002 | Kiy et al. |
| 6,410,281 B1 | 6/2002 | Barclay |
| 6,433,152 B1 | 8/2002 | Lang et al. |
| 6,451,567 B1 | 9/2002 | Barclay |
| 6,509,178 B1 | 1/2003 | Tanaka et al. |
| 6,566,123 B1 | 5/2003 | Barclay |
| 6,582,941 B1 | 6/2003 | Yokochi et al. |
| 6,596,766 B1 | 7/2003 | Igarashi et al. |
| 6,607,900 B2 * | 8/2003 | Bailey et al. ............ 435/134 |
| 6,977,167 B2 | 12/2005 | Barclay |
| 7,005,280 B2 | 2/2006 | Barclay |
| 7,011,962 B2 | 3/2006 | Barclay |
| 7,022,512 B2 | 4/2006 | Barclay |
| 7,033,584 B2 | 4/2006 | Barclay |
| 7,208,160 B2 | 4/2007 | Katzen |
| 7,381,558 B2 | 6/2008 | Barclay |
| 7,579,174 B2 * | 8/2009 | Bailey et al. ............ 435/134 |
| 5,340,742 C1 | 2/2010 | Barclay |
| 5,518,918 C1 | 2/2010 | Barclay |
| 6,566,123 C1 | 3/2010 | Barclay |
| 7,732,170 B2 | 6/2010 | Bailey et al. |
| 2003/0180898 A1 | 9/2003 | Bailey et al. |
| 2006/0094089 A1 | 5/2006 | Barclay |
| 2006/0160203 A1 | 7/2006 | Barclay |
| 2006/0188969 A1 | 8/2006 | Barclay |
| 2006/0286648 A1 | 12/2006 | Bailey et al. |
| 2006/0286649 A1 | 12/2006 | Bailey et al. |
| 2007/0082384 A1 | 4/2007 | Barclay |
| 2007/0099280 A1 | 5/2007 | Barclay |
| 2008/0032360 A1 | 2/2008 | Bailey et al. |
| 2008/0032361 A1 | 2/2008 | Bailey et al. |
| 2008/0032362 A1 | 2/2008 | Bailey et al. |
| 2008/0032363 A1 | 2/2008 | Bailey et al. |
| 2008/0032364 A1 | 2/2008 | Bailey et al. |
| 2008/0032365 A1 | 2/2008 | Bailey et al. |
| 2008/0032366 A1 | 2/2008 | Bailey et al. |
| 2008/0032381 A1 | 2/2008 | Bailey et al. |
| 2008/0057551 A1 | 3/2008 | Bailey et al. |
| 2008/0166780 A1 | 7/2008 | Barclay |
| 2008/0175953 A1 | 7/2008 | Barclay |
| 2008/0199923 A1 | 8/2008 | Barclay |
| 2009/0081465 A1 | 3/2009 | Morgenstern et al. |

FOREIGN PATENT DOCUMENTS

| | | | |
|---|---|---|---|
| AU | 687016 B2 | 2/1998 |
| CA | 2072978 C | 5/1991 |
| CA | 2563427 | 10/2005 |
| DE | 3213744 A1 | 11/1982 |
| DE | 3603000 A1 | 8/1987 |
| DE | 3920679 A1 | 1/1991 |
| DE | 19838011 | 5/1999 |
| DE | 102004017370.2 | 10/2005 |
| EP | 193926 | 9/1986 |
| EP | 0231904 B1 | 8/1987 |
| EP | 0404058 B1 | 12/1990 |
| EP | 0823475 | 2/1998 |
| EP | 1024199 | 8/2000 |
| FR | 1557635 A | 2/1969 |
| GB | 857161 | 12/1960 |
| GB | 1123884 | 8/1968 |
| GB | 1143405 | 2/1969 |
| GB | 1401956 | 8/1975 |
| GB | 1466853 A | 3/1977 |
| GB | 2098065 A | 11/1982 |
| JP | 54-105081 A | 8/1979 |
| JP | 58-196068 A | 11/1983 |
| JP | 58-213613 A | 12/1983 |
| JP | 60-087798 A | 5/1985 |
| JP | 60-105471 A | 6/1985 |
| JP | 61-170366 A | 8/1986 |
| JP | 63-040711 A | 2/1988 |
| JP | 63-237745 A | 10/1988 |
| JP | 1-215245 A | 8/1989 |
| JP | 02-171127 | 7/1990 |
| JP | B H 03-071100 | 11/1991 |
| JP | 4-58847 A | 2/1992 |
| JP | 4-152861 A | 5/1992 |
| JP | 4-252145 A | 9/1992 |
| JP | 4-271754 A | 9/1992 |
| JP | WA H05-503425 | 6/1993 |
| JP | WA H05-505726 | 8/1993 |
| JP | A H 06-209718 | 8/1994 |
| JP | A H 06-237703 | 8/1994 |
| JP | A H 07-255387 | 10/1995 |
| JP | 08-502405 | 3/1996 |
| JP | H08-509355 | 10/1996 |
| JP | A H 08-322475 | 12/1996 |
| JP | A H09-000284 | 1/1997 |
| JP | A H09-065871 | 3/1997 |
| JP | A HEI09-084590 | 3/1997 |
| JP | A HEI09-110888 | 4/1997 |
| JP | A H11-285376 | 10/1999 |
| KR | 1994-7396 | 8/1994 |
| WO | WO 88/02989 A1 | 5/1988 |
| WO | WO 88/10112 A1 | 12/1988 |
| WO | WO 89/00606 A1 | 1/1989 |
| WO | WO 91/07498 A1 | 5/1991 |
| WO | WO 91/11918 | 8/1991 |
| WO | WO 91/14427 | 10/1991 |
| WO | WO 92/12711 A1 | 8/1992 |
| WO | WO 92/13086 | 8/1992 |
| WO | WO 94/08467 | 4/1994 |
| WO | WO 96/38051 A1 | 12/1996 |
| WO | WO 98/03671 | 1/1998 |
| WO | WO 98/37179 | 8/1998 |
| WO | WO 98/55625 | 12/1998 |
| WO | WO 99/24448 | 5/1999 |
| WO | WO 01/54510 A1 | 8/2001 |
| WO | WO 01/60166 A1 | 8/2001 |
| WO | WO 02/083870 | 10/2002 |
| WO | WO 2004/087879 | 10/2004 |
| WO | WO 2005/097982 | 10/2005 |

OTHER PUBLICATIONS

Holden C. Science, Dec. 1998. vol. 282, p. 1983.

Hopwood et al. "Molecular Genetics of Polyketides and its Comparison to Fatty Acid Biosynthesis", Ann. Rev. Genet. 1990, vol. 24, pp. 37-66.

Hutchinson, Microbial polyketide synthases: more and more prolific, Proc Natl Acad Sci U S A. Mar. 30, 1999;96(7):3336-8.

Jones et al.; "Recent Advances in Aquatic Mycology; Chapter 10: Physiology of Marine Phycomycetes";John Wiley & Sons; 1976, pp. 261-278.

Kealy et al.; "Production of a polyketide natural product in nonpolyketide-producing prokaryotic and eukaryotic hosts"; Proc. Natl. Acad. Sci. USA; Jan. 1998; vol. 95; pp. 505-509.

Kendrick et al.; "Lipid formation in the oleaginous Mould Entomophthoro Exitalis Grown in Continuous Culture: Effects of Growth Rate, Temperature and Dissolved Oxygen Tention on Polyunsaturated Fatty Acids"; Appl. Microbial Biotechnol; 1992; vol. 37, pp. 18-22.

Lewis et al.; "The Biotechnological Potential of Thraustochytrials"; Mar Biotechnol (NY); Nov. 1999; vol. 6; pp. 580-587.

Metz et al.; "Production of Polyunsaturated Fatty Acids by Polyketide Synthases in Both Prokaryotes and Eukaryotes"; Science; Jul. 13, 2001; vol. 293; pp. 290-293.

Qiu, Biosynthesis of docosahexaenoic acid (DHA, 22:6-4, 7,10,13,16,19): two distinct pathways, Prostaglandins Leukot Essent Fatty Acids. Feb. 2003;68(2):181-6.

Science and Technology of Food Industry, Issue No. 6, 1999, pp. 62-63.

Sogin et al., Stramenopiles, 1995. Obtained from http://ag.arizona.edu/tree/eukaryotes/stramenopiles/stramenopiles.html on Mar. 7, 2001.

Wallis et al.; "Polyunsaturated Fatty Acids Synthesis: What Will They Think of Next?"; Trends in Biochemical Sciences; Sep. 2002; vol. 27, No. 9; pp. 467-473.

Wetzel, in Limnology, W.B. Saunders Company, Philadelphia, 1975, pp. 123-125.

Yamauchi et al. J. Ferment. Technol. 1983. vol. 61, No. 3, pp. 275-280.

Yazawa et al.; "Chapter 3: Production of Eicosapentaenoic Acid from Marine Bacteria"; Sagami Chemical Research Center; 1992; pp. 29-51.

Babij, Effects of Oxygen and Glucose Levels on Lipid Composition of Yeast Candida utils Grown in Continuous Culture, vol. XI Biotechnology and Bioengineering at 593-603 (1969).

Plaintiff Martek Biosciences Corporation's Opening Claim Construction Brief, in Civil Action No. 03-089-GMS, dated Oct. 11, 2005, 44 pages.

Defendant Nutrinova's Opening Brief Regarding Claim Construction of Disputed Terms, in Civil Action No. 03-089-GMS, dated Oct. 11, 2005, 39 pages.

Plaintiff Martek Biosciences Corporation's Answering Claim Construction Brief, in Civil Action No. 03-089-GMS, dated Nov. 2, 2005, 47 pages.

Defendant Nutrinova's Reply Brief in Response to Plaintiff Martek's Opening Claim Construction Brief, in Civil Action No. 03-089-GMS, dated Nov. 2, 2005, 24 pages.

Singh et al. "Production of high yields of docosahexaenoic acid by *Thraustochytrium roseum* ATCC 28210". Journal of Industrial Microbiology (1996), vol. 16, No. 6, pp. 370-373.

Shinmen et al. "Concentration of eicosapentaenoic acid and docosahexaenoic acid in an arachidonic acid-producing fungus Mortierella alpina 1S-4, grown with fish oil". Applied Microbiology and Biotechnology. 1992, vol. 38, No. 3, pp. 301-304.

Chi et al. "Study of a two-stage growth of DHA-producing marine algae *Schizochytrium limacinum* SR21 with shifting dissolved oxygen level" Appl. Microbiol. Biotechnol. 2009, 81 :1141-1148.

Ahmad, I. and J. Hellebust, "Osmoregulation in the Extremely Euryhaline Marine Micro-alga *Chlorella autotrophica,*" *Plant Physiol. 74*:1010-1015, American Society of Plant Physiologists, United States (1984).

Drapeau, G., et al., "Nutrition and Metabolism of Marine Bacteria. XV. Relation of Na+-activated transport to the Na+ requirement of a marine pseudomonad for growth," *J. Bacteriol. 92*:63-71, American Society for Microbiology, United States (1966).

Hellebust, J., "A comparative study of sodium and osmotic requirements for growth and nutrient uptake of two related green flagellates, *Dunaliella tertiolecta* and *Chlamydomonas pulsatilla,*" *Arch. Microbiol. 143*:11-14, Spring-Verlag, Germany (1985).

Sguros, P. and J. Simms, "Role of Marine Fungi in the Biochemistry of the Oceans. IV. Growth Responses to Seawater Inorganic Macroconstituents," *J. Bacteriol. 88*:346-355, American Society for Microbiology, United States (1964).

Barclay, W., et al., "Heterotrophic production of long chain omega-3 fatty acids utilizing algae and algae-like microorganisms," *J. Appl. Phycol. 6*:123-129, Kluwer Academic Publishers, Belgium (1994).

Kyle, D., "Market applications for microalgae," *J. Am. Oil Chem. Soc. 66*:648-651, American Oil Chemists Society, United States (1989).

Siegenthaler, et al.; "Phosphate Uptake in an Obligately Marine Fungus, II. Role of Culture Conditions, Energy Sources and Inhibitors"; Journal of Bacteriology; Apr. 1967; vol. 94, No. 4; pp. 1281-1288.

Nichols, et al.; "Anaerobic production of polyunsaturated fatty acids by *Shewanella putrefaciens* strain ACAM 342", FEMS Microbiology Letters; 1992; vol. 98; 117-122.

Richmond, A. ed., "CRC Handbook of Microalgal Mass Culture," CRC Press, Inc., Boca Raton, Florida, 344-398 (1986).

Aaronson et al., "Microalgae as a Source of Chemicals and Natural Products," 14 pages, Elsevier, (1980).

Abbildungen aus Porter, D., S. 393, "Wachstums- und Entwicklungsstadien von Thraustochytriaceae," 1 page (1990).

Abril and Barclay, "Production of Docosahexaenoic Acid-Enriched Poultry Eggs and Meat Using an Algae-Based Feed ingredient," *The Return of o3 Fatty Acids into the Food Supply. I. Land-Based Animal Food Products and Their Health Effects* 83: 77-88, Simopoulos AP (ed), World Rev Nutr Diet. Basel, Karger (1998).

Affidavit of Mr. Rosing, "Eidesstattlich Versicherung," 1 page (with computer translation) (Mar. 23, 2010).

Ainsworth, "Introduction and Keys to Higher Taxa.," 1-7 in The Fungi. An Advanced Treatise, vol. 4B, G.C. Ainsworth et al. eds., Academic Press (1973).

Ajuyah et al., "Dietary Antioxidants and Storage Affect Chemical Characteristics of w-3 Fatty Acid Enriched Broiler Chicken Meats," J. Food Sci., 1993, 58(1), 43-46.

Ajuyah et al., "Studies on canola seed in turkey grower diet: Effects on w-3 fatty acid composition of breast meat, breast skin and selected organs," Can. J. Anim. Sci., 73: 177-181 (1993).

Akimoto et al., "Metal Salts Requisite for the Production of Eicosapentaenoic Acid by a Marine Bacterium Isolated from Mackerel Intestines," *JAOCS* 68: 504-508 (1991).

Akimoto et al., "Production of Eicosapentaenoic Acid by a Bacterium Isolated from Mackerel Intestines," *JAOCS*, 67(12): 911-915 (Dec. 1990).

Ando et al., "Incorporation of n-3 Polyunsaturated Fatty Acids into Phospholipids of a Marine Bacterium *Vibrio* sp. Cultivated with Sardine Oil," *J. Ferm. Bioeng.* 73: 169-171, (1992).

Author unknown, "Calculation of sodium content according to Example 8 of Dl" 1 page (Sep. 15, 2005).

Author unknown, "Eggs Developed That Don't Boost Cholesterol," *Investors Daily* (May 3, 1988).

Bahnweg et al., "A New Approach to Taxonomy of the Thraustochytriales and Labyrinthulales," 131-140, in The Biology of Marine Fungi, S.T. Moss ed., Cambridge University Press (1986).

Bahnweg et al., "Four New Species of Thraustochytrium From Antarctic Regions, with Notes on the Distribution of Zoosporic Fungi in the Antarctic Marine Ecosystems," *Amer. J. Bot.*, 61(7): 754-766 (1974).

Bahnweg, "Studies on the Physiology of Thraustochytriales," *Veroff. Inst. Meeresforsch. Bremerh.*, 17: 245-268 (1979).

Bajpai et al., "Effects of Aging *Mortierella mycelium* on Production of Arachidonic and Eicosapentaenoic Acids," *JAOCS* 68: 775-780, (Oct. 1991).

Bajpai et al., "Eicosapentaenoic Acid (EPA) Formation; Comparative Studies with *Mortierella* Strains and Production by *Mortierella* elongate," *Mycol. Res.* 95: 1294-1298 (1991).

Bajpai et al., "Optimization of Production of Docosahexaenoic Acid (DHA) by *Thraustochytrium aureum* ATCC 34304," *JAOCS* 68: 509-514, (Jul. 1991).

Bajpai et al., "Production of Docosahexaenoic Acid by *Thraustochytrium aureum,*" Appl. Microbiol. Biotechnol. 35: 706-710 (1991).

Barlow and Pike, "Humans, animals benefit from omega-3 polyunsaturated fatty acids," *Feedstuffs* 18-26 (May 13, 1991).

Barr, J. S. "The phylogenetic and taxonomic implications of flagellar rootlet morphology among zoosporic fungi," *BioSystems* 14: 359-370 (1981).

Barr, J. S. "The zoosporic grouping of plant pathogens," 43-83, in *Zoosporic Plant Pathogens: a modern perspective*, S. T. Buczacki (ed.), Academic Press, (1983).

Bartnicki-Garcia, "The Cell Wall: A Crucial Structure in Fungal Evolution," 389-403, in *Evolutionary Biology of the Fungi*, A.D.M. Rayner et al. eds., Cambridge University Press (1998).

Beach et al., "Biosynthesis of Oleic Acid and docosahexaenoic Acid by a Heterotrophic Marine Dinoflagellate *Crypthecodinium cohnii*," *Biochimica et Biophysica Acta*. 369: 16-24 (1974).

Behrens et al., "Eicosapentaenoic Acid from Microalgae," *Chemical Abstracts* vol. 111(21): 623, col. 2, abstract No. 193025d (Nov. 20, 1989).

Behrens et al., "Eicosapentaenoic Acid from Microalgae," *Novel Microb. Prod. Med. Agric* 253-259 (1989).

Bell and Henderson, "Molecular Species Composition of Phosphatidylcholine from *Crypthecodinium cohnii* in Relation to Growth Temperture," *Lipids* 25(2): 115-118 (1990).

Berrio et al. "Effect of Corn, Linseed and Menhaden Fish Oils on the Fatty Acid Pattern of Broiler Thigh Muscle," Abstract of the 8th Ann. Meeting, *Poultry Science* vol. 66(Supp. 1): 66 (1987).

Bingham et al. "Production of Specialty Lipids by Microalgae," Program and Abstracts of the 46th Annual Meeting of the Society for Industrial Microbiology, 122 (Aug. 13-18, 1989).

Borowitzka and Borowitzka, *"Dunaliella," Algal Biotechnology*, 27-58, Cambridge University Press, London (1988).

Borowitzka and Borowitzka, *Micro-Algal Biotechnology*, 257-287, Cambridge University Press, London (1988).

Borowitzka, "Microalgae as Sources of Essential Fatty Acids," *Australian Journal of Biotechnology* 1: (4)58-62 (Mar. 1988).

Boswell et al., "SCO Production by Fermentative Microalgae," 274-286, in *Industrial Applications of Single Cell Oils*, Kyle et al., eds., American Oil Chemists' Society, Champaign, III (1992).

Bremer "Physiological responses of some thraustochytrid fungi," *Veroff. Inst. Meeresforsch. Bremerhaven* Suppl. 5: 237-250 (1974).

Britton et al., "Shore Ecology of the Gulf of Mexico," 183 University of Texas Press, Austin (1989).

Bronsgeest-Schoute, et al., "The effect of various intakes of omega-3 fatty acids on the blood lipid composition in healthy human subjects," *American Journal of Clinical Nutrition* 34: 1752-1757 (Sep. 1981).

Carlson, et al., "Effect of Fish Oil Supplementation on the n-3 Fatty Acid Content of Red Blood Cell Membranes in Preterm Infants," *Pediatric Research* 507-510 (1987).

Cavalier-Smith, "The Origin of Nuclei and of Eukaryotic Cells," *Nature* 256: 463-468 (1975).

Cavalier-Smith, T., "A 6-kingdom classification and a unified phylogeny" 1027-1034, in *Endocytobiology II: Intracellular Space as Oligogenetic System*, H. E. A. Schenk and W. Schwemmler (eds.), De Gruyter (Berlin) (1983).

Cerda-Olmeda et al., "A Biography of Phycomyces," 7-26, in *Phycomyces*, Cerda-Olmeda et al. eds., CSH Laboratory (1987).

Chamberlain, A. H. and Moss, S. T. "The thraustochytrids: a protist group with mixed affinities," *BioSystems* 21: 341-349 (1988).

Chen et al. "C-Labeled fatty acids from microalgae," *Developments in Industrial Microbiology, Journal of Industrial Microbiology* 31(Suppl. No. 5): 257-264 (1990).

Chen et al. "Effect of C/N ratio and aeration on the fatty acid composition of heterotrophic *Chlorella sorokiniana*," *Journal of Applied Phycology* 3: 203-209 (1991).

Cherian and Sim, "Effect of Feeding Full Fat Flax and Canola Seeds to Laying Hens on the Fatty Acid Composition of Eggs, Embryos, and Newly Hatched Chicks," *Poultry Sci.* 70: 917-922 (1991).

Chu, et al, "Polyunsaturated Fatty Acids and Neutral Lipids in Developing Larvae of the Oyster *Crassostrea virainica*," *Lipids* 19(11): 815-820 (1984).

Cohen and Ratlege, "Single Cell Oils," pp. 36-51 (2005).

Cohen et al. "Effect of environmental conditions on fatty acid composition of the red alga *Porphyridium cruentum*: correlation to growth rate," *J. Phycol*. 24: 328-332 (1988).

Cohen et al., "Overproduction of .gamma.-Linolenic and Eicosapentaenoic Acids by Algae," *Plant Physiol*.98: 569-572 (1992).

Cole-Parmer Catalog, 1999-2000, pp. 124-130 and cover.

Combs, "Algae (*Chlorella*) as a Source of Nutrients for the Chicks," *Science* 116: 453-454 (1952).

Couch et al., "Effect of Diet on Triglyceride Structure and Composition of Egg Yolk Lipids," *Lipids* 8(7): 385-392 (1973).

Cruickshank, "Studies in Fat Metabolism in the Fowl," *Biochem. J.*, 28: 965-977 (1934).

Dansky, "The Growth Promoting Properties of Menhaden Fish Oil as Influenced by Various Fats," *Poultry Sci*. 41: 1352-1354 (1962).

Dick, "Saprolegniales," 113-144, in *The Fungi. An Advanced Treatise*, G.C. Ainsworth et al. eds., Academic Press (1973).

P. Singleton and D. Sainsbury, *Dictionary of Microbiology and Molecular Biology* 406-408 and 332 (1978).

Edwards, Jr. and May, "Studies with Menhaden Oil in Practical-Type Broiler Rations," *Poultry Sci*. 44: 685-688 (1965).

Edwards, Jr. et al., "Carcass Composition Studies. 1. Influences of Age, Sex and Type of Dietary Fat Supplementation on Total Carcass and Fatty Acid Composition," *Poultry Sci*. 52: 934-948 (1972).

Ellenbogen, "Polyunsaturated Fatty Acids of Aquatic Fungi: Possible Phylogenetic Significance," *Comp. Biochem. Physiol*. 29: 805-811 (1969).

Emerson, "Current Trends of Experimental Research in the Aquatic Phycomycetes," pp. 169-200, 1950, Ann. Rev. Micro., vol. 4.

Encyclopedia of Chemical Technology, Third Edition, vol. 11, John Wiley & Sons, pp. 164-178 (1980).

Erwin, "Comparative Biochemistry of Fatty Acids in Eukaryotic Microorganisms," 41-143, in *Lipids and Biomembranes of Eukaryotic Microorganisms*, J. Erwin ed., Academic Press (1973).

Facciotti D. et al., "Cloning and Characterization of Polyunsaturated Fatty Acids (PUFA) Genes from Marine Bacteria," *Abstracts of the International Symposium on progress and prospectives of Marine Biotechnology*, Qingdao, China (Oct. 5-10, 1998).

Falbe, J. et al. *Rompp Chemie Lexikon* 286-287 (1990).

Findlay et al., "Biochemical Indicators of the Role of Fungi and Thraustrochytrids in Mangrove Detrital Systems," 91-103, in *The Biology of Marine Fungi*, S.T. Moss ed., Cambridge University Press (1986).

Fink, "Corrosion of Metals in Seawater," *OSW Research and Development Progress Report No. 46* (Dec. 1960).

Fisher et al., "Observations on the Cholesterol, Linoleic and Linolenic Acid Content of Eggs as Influenced by Dietary Fats," *J. Nutr*. 63: 119-129 (1957).

Flannery et al., "Salt Desideratum of Vibro Costicolus. an Obligate Halophilic Bacterium I. Ionic Replacement of Sodium Chloride Requirement," *Journal of Bacteriol*. 64(5): 713-717 (1952).

Fogg, G.E. *Algal Cultures and Phytoplankton Ecology*, 2nd ed., 90-91, The University of Wisconsin Press (1975).

Fry et al., "Fish Meal Studies. 2. Effects of Levels and Sources on "Fishy Flavor" in Broiler Meat," *Poultry Sci*. 44: 1016-1019 (1965).

Fuller, et al., "Isolation and Pure Culture Study of Marine Phycomycetes," *Mycologia* 56: 745-756 (1964).

Gaertner, "Eine methode des quantitativen Nachweises niederer, mit Pollen Koderbarer Pilze im Meerwasser und im Sediment" *Veroff. Inst. Meeresforsch. Bremerh*. Suppl. 3: 75-92 (1968).

Gaertner, A., *Helgol. Wiss. Meeresuntersuchungen* 15: 181-186 (Translated abstract) (1967).

Gaertner, A., *Veroff. Inst. Meeresforsch. Bremerh*. 12: 321-327 (Translated abstract) (1970).

Gaertner, A., *Veroff. Inst. Mereresforsch. Bremerh*. 19: 61-69 (Translated abstract) (1981).

Galvin et al., "Effect of dietary oil quality and alpha-tocopherol supplementation on the oxidative stability of broiler tissues," *Proc. Nutrition Soc*. 53(2): 13A (1994).

Gandhi et al., "Production of the Polyunsaturated Fatty Acids Arachidonic Acid and Eicosapentaenoic Acid by the Fungus *Pythium ultimum*," *J. Gen. Microbiol*. 137: 1825-1830 (1991).

Jones, et al., "Physiology of Marine Phycometes" Elek Science, 261-278 (1976).

Garrill et al., "Preliminary observations on the monovalent cation relations of *Thraustochytrium aureum*, a fungus requiring sodium for growth," *Mycol. Res.* 96(4): 295-304 (1992).

Gellerman et al., "Methyl-Directed Desaturation of Arachidonic to Eicosapentaenoic Acid in the Fungus, *Saprolegnia parasitica*," *Biochim. Biophys. Acta.* 573: 23-30 (1979).

Goldstein et al., "Axenic Culture Studies of a New Marine Phycomycete Possessing an Unusual Type of Asexual Reproduction," *Am. J. Bot.* 51(1): 72-78 (1964).

Goldstein et al., "Biology of a Problematic Marine Fungus, *Dermocystidium* sp. I. Development and Cytology," *Archiv for Mikrobiologie* 53.1: 1-11 (1966).

Goldstein et al., "Biology of a Problematic Marine Fungus, *Dermocystidium* sp. II. Nutrition and Respiration," *Mycologia* 61: 468-472 (1969).

Goldstein, "Development and Nutrition of New Species of *Thraustochystrium*," *Am. J. Bot.* 50: 271-279 (1963).

Goldstein, S. "Morphological Variation and Nutrition of a New Monocentric marine Fungus" *Arch. Mikrobiol.* 45: 101-110 (1963 b).

Goldstein, S. "Studies of a New Species of *Thraustochytrium* that Displays Light Stimulated Growth," *Mycologia* 55(6): 799-805 (1963).

Granger et al., "Kinetics of Growth and Fatty Acid Production of *Rhodotorula glutinis*," *Appl. Microbiol. Biotechnol.* 37: 13-17 (1992).

Greasham et al. "Nutritional Improvement of Processes," 41-42, from *Manual of Industrial Microbiology and Biotechnology*, Demain and Solomon, Eds, American Society for Microbiology, Washington, D.C. (1986).

Hansen et al., "Effects of Culture Conditions on Accumulation of Arachidonic and Eicosapentaenoic Acids in Cultured Cells of *Rhytidiadelphus squarrosus* and *Eurhynchium striatum*," *Phytochemistry* 30: 1837-1841 (1991).

Hargis, "Designing Eggs for the Health Conscious Consumer," *Egg Industry* 24-30 (Nov./Dec. 1992).

Harrington et al. "The Polyunsaturated Fatty Acids of Marine Dinoflagellates," *J. Protozool* 17(2): 213-219 (1970).

Harrington et al., "The monoenoic and docosahexaenoic fatty acids of a heterotrophic dinoflagellate," *Biochim. Biophys. Acta.* 164: 137-39 (1968).

Harris, et al., "Will dietary omega-3 fatty acids change the composition of human milk," *American Journal of Clinical Nutrition* 40: 780-785 (Oct. 1984).

Harwood, "Plant Acyl Lipids: Structure, Distribution, and Analysis" 2-48, in *The Biochemistry of Plants*, vol. 4, Academic Press, Inc. (1980).

Haskins et al., "Steroids and the Stimulation of Sexual Reproduction of a Species of *Pythium*," *Canadian J. Microbiology* 10: 187-195 (1964).

Henderson et al., "Lipid Composition and Biosynthesis in the Marine Dinoflagellate *Crypthecodinium cohnii*," *Phytochemistry* 27(6): 1679-1683 (1988).

Holliday, FGT "4. Salinity, 4.3 Animals. 4.32 Fishes." 997-1083, in *Marine Ecology, vol. 1 Environmental Factors, Part 2*, O. Kinne (ed), John Wily and Sons, London (1971).

Holliday, "Salinity." 997, 1023-1025, in *Marine Ecology*, vol. 1, Part 2 Kinne, ed. (1971).

Honda, D. et al. "*Schizochytrium limacinum* sp. nov., a new thraustochytrid from a mangrove area in the west Pacific Ocean" *Mycol. Res.* 102(4): 439-448 (1998).

Hori and Osawa "Evolutionary change in 5SrRNA secondary structure and a phylogenetic tree of 352 5S rRNA species," *Biosystems* 19: 163-172 (1986).

Hori et al., "The Nucleotide Sequence of 5S rRNA from a Cellulai Slime Mold *Dictyostelium discoideum*," *Nucl. Acids Res.* 8:5535-5539 (1980).

Horne, R.A., *Marine Chemistry*, 150-163 and 486-487, Wiley & Sons (1969).

Hulan and Proudfoot, "Replacement of Soybean Meal in Chicken Broiler Diets by Rapeseed Meal and Fish Meal Complementary Sources of Dietary Protein," *Can. J. Anim. Sci.* 61:999-1004 (1981).

Hulan et al., "Omega-3 Fatty Acid Levels and General Performance of Commercial Broilers Fed Practical Levels of Redfish Meal," *Poultry Sci.* 68:153-162 (1989).

Hulan et al., "The Broiler Chicken as an Alternative to Fish and Shellfish as a Dietary Source of Eicosapentaenoic Acid," Abstract of the 75th Ann. Meeting *Poultry Sci.* 65 (Suppl.): 60 (1986).

Hulan et al., "The Effects of Different Dietary Fat Sources on General Performance and Carcass Fatty Acid Composition of Broiler Chickens," *Poultry Sci.* 63: 324-332 (1984).

Hulan et al., "The Effects of Feeding Fish Meal on the General Performance, Omega-3 Fatty Acid Composition and sensory Characteristics of Broiler Chickens," Abstract of the 8th Ann. Meeting, *Poultry Science*, 66(1): 117 (1987).

Hunter, "Fish Oil and Other Omega-3 Sources," *J. Am. Oil Chem. Soc.* 64: 1592-1596 (1987).

Illingworth, et al., "Inhibition of low density lipoprotein synthesis by dietary omega-3 fattv acids in humans," *Arterioscler. Throm. Vasco Biol.* 270-275, (1984).

Imhoff et al., "Requirements for, and Cytoplasmic Concentrations of, Sulphate and Chloride, and Cytoplasmic Volume Spaces in the Halophilic Baterium *Ectothiorhodospira mobilis*," *Journal of General Microbiology*, 135:237-244 (1989).

*International Dictionary of Medicine and Biology*, 1042 and 1267 (1986).

Jennings "Some Aspects of the Physiology and Biochemistry of Marine Fungi," *Biol. Rev.* 58: 423-459 (1983).

Jong et al., "American Type Culture Collection Catalogue of Fungi/Yeast," 350 and 378, American Type Culture Collection, 17th Edition (1987).

Karleskind (ed), *Oils and Fats Manual*, vol. 1, 67-68 and 81 (1996).

Kates, "Techniques of Lipidology: Isolation, Analysis and Identification of Lipids," *Laboratory Techniques in Biochemistry and Molecular Biology* 3: 186-278 (1986).

Kazama, F "The zoospore of *Schizoshytrium aggregatum*," *Can J. Bot.* 58: 2434-2446 (1980).

Kendrick et al., "Lipids of Selected Molds Grown for Production of n-3 and n-6 Polyunsaturated Fatty Acids," *Lipids* 27(1):15-20 (1992).

Kendrick et al., "Microbial Polyunsaturated Fatty Acids of Potential Commercial Interest," *SIM Industrial Microbiology News* 42:59-65 (1992).

Kinne, *Marine Ecology*, vol. 1, Part 2, 821-995 (1971).

Kinne, *Marine Ecology*, vol. 1, Part 2, 405-524 (1970).

Kinne, *Marine Ecology*, vol. 1, Part 1, 820-823, 876-885, 940-941, 952-953 (1970).

Kinne, *Marine Ecology*, vol. 3, Part 2, 584-591 (1977).

Kinne, "Temperature", 407, 430, 431, 432, 433, In *Marine Ecology*, vol. 1, Part 2 (1971).

Klausner "Algaculture: Food for Thought," *BioTechnology* 4: 947-948 and 952-953, (Nov. 1986).

Kohlmeyer et al., *Marine Mycology*, 2-3 (1979).

Krogdahl, "Digestion and Absorption of Lipids in Poultry," *J. Nutrition* 115:675-685 (1985).

Kyle et al. "Microalgae as a Source of EPA," 161-169, presented at the International Composium for New Aspects of Dietary Lipids and Uses at the University of Phos., Sweden (1989).

Kyle et al., "Bioproduction of Docosahexaenoic Acid (DHA) by Microalgae," 287-300, in *Industrial Applications of Single Cell Oils*, Kyle et al., eds., American Oil Chemists' Society, Champaign, IL (1992).

Kyle et al., "Microalgae as a Source of EPA-Containing Oils," pp. 117-121, 1988, Proc.-World Conf. Biotechnol. Fats Oils Ind.

Kyle, "Microalgae as a Source of EPA-Containing Oils," *J. Am. Oil Chem. Soc.* 64: 1251 (1987).

Kyle, "Microalgae as a Source of EPA-Containing Oils," *Chemical Abstracts* 111(3):495, col. 2, abstract No. 22136 (Jul. 17, 1989).

Lee et al., "Distribution of 21: 6 Hydrocarbon and its Relationship to 22: 6 Fatty Acid in Algae" *Phytochemistry* 10: 593-602 (1971).

Leedale, G. "How many are the kingdoms of organisms," *Taxon* 23: 261-270 (1974).

Lepage et al., "Improved Recovery of Fatty Acid Through Direct Transesterification Without Prior Extraction or Purification," *J. Lipid Res.* 25: 1391-1396, (1984).

Leskanich and Noble, "Manipulation of the n-3 polyunsaturated fatty acid composition of avian eggs and meat," *World's Poultry Science Journal* 53: 155-183 (1997).
Letter from Dr. Schaumann, "Kulturoptimierung von Thraustochytriales in verdunnten Meerwasser-enthaltenden Nahrlosungen," 1 page (Dec. 7, 2000).
Letter from Dr. Schaumann, "Salinitats- bzw. Leitfahigkeitsmessungen," 2 pages (Dec. 7, 2000).
Leveille et al., "Protein Value .And the Amino Acid Deficiencies of Various Algae for Growth of Rats and Chicks," *J. Nutrition* 76: 423-428 (1962).
Lewis et al., "Production of Polyunsaturated Fatty Acids by Australian Thraustochytrids: Aquaculture Applications" from "Hatchery feeds for aquaculture" *Proceedings of a workshop held in Cairns* (Mar. 9-10, 2000).
Lipstein et al., "The Nutritional and Economic Value of Algae for Poultry," 667-685, in *Algae Biomass*, G. Shelef and C.J. Soeder, eds., Elsevier/North-Holland Biomedical Press (1980).
Lipstein et al., "The Nutritional Value of Algae for Poultry. Dried Chlorella in Broiler Diets," *Br. Poultry Sci.* 21: 9-21 (1980).
Lipstein et al., "The Nutritional Value of Algae for Poultry. Dried Chlorella in Layer Diets," *Br. Poultry Sci.* 21: 23-27 (1980).
Liu et al, "Increase in Plasma Phospholipid Docosahexaenoic and Eicosapentaenoic Acids as a Reflection of their Intake and Mode of Administration," *Pediatric Research*, 292-296 (1987).
Loosanoff, V., "On behavior of oysters transferred from low to high salinities," *Anatomical Record* 108: 579 (1950).
Lovell "Increasing Omega-3 Fatty Acids in Farmed Catfish," *Aquaculture Magazine* 54-55 (Sep./Oct. 1988).
Mackereth et al., *Water Analyses*, 47-49 (1978).
MacLeod et al., "Nutrition and Metabolism of Marine Bacteria, I: Survey of Nutritional Requirements," *J. Bactiol.* 68: 680-686 (1954).
MacLeod et al., "Nutrition and Metabolism of Marine Bacteria II: Observations on the Relation of Sea Water to the Growth of Marine Bacteria," 661-667 (1956).
MacLeod, "Nutrition and Metabolism of Marine Bacteria, VI. Quantitative Requirements for Halides, Magnesium, Calcium, and Iron," *Can. J. Microbiol.* 3: 753-759 (1957).
MacLeod, "Nutrition and Metabolism of Marine Bacteria. III. The Relation of Sodium and Potassium to Growth," *J. Cell Comp. Physiol.* 50: 389-393 (1957).
MacLeod, "The Question of the Existence of Specific Marine Bacteria," *Bacteriological Reviews* 29:9-23 (Mar. 1965).
Mannella et al., "Interrelatedness of 5S RNA Sequences Investigated by Correspondence Analysis," *J. Mol. Evol.* 24: 228-235 (1987).
Margulis, L. and Sagan, D. "Order amidst animalcules: the Proctoctista kingdom and its undulipodiated cells." *BioSystems* 18: 141-147 (1985).
Marion and Woodroof, "The Fatty Acid Composition of Breast, Thigh, and Skin Tissues of Chicken Broilers as Influenced by Dietary Fats," *Poultry Sci.* 42: 1202-1207 (1963).
Markson LabSales, *Master Catalog,* pp. 65-69 and cover (1998).
MaxEPA data sheet, available at http://www.vitabase.com/supplements/essential-fatty-acids/maxepaomega3.aspx, pp. 1-3 (printed Oct. 19, 2009).
McLachlan, "Some Considerations of the Growth of Marine Algae in Artificial Media," *Canadian Journal of Microbiology* 10: 769-782 (1964).
McLeod, "Nutritional Factors Influencing Carcass Fat in Broilers—A Review," *World's Poultry Science Journal* 37: 194-200 (1981).
McLusky D. *The Estuarine Ecosystem* 2nd Ed., 104-105, Chapman and Hall, New York (1989).
Metting "Microalgae Applications in Agriculture," Program and Abstracts of the 46th Annual Meeting of the Society for Industrial Microbiology,122 (Aug. 13-18, 1989).
Miller and Robisch, "Comparative Effect of Herring, Menhaden, and Safflower Oils on Broiler Tissues Fatty Acid Composition and Flavor," *Poultry Sci.*, 48: 2146-2157 (1969).
Miller et al., "Dietary Effect of Menhaden-Oil Ethyl Esters on the Fatty Acid Pattern of Broiler Muscle Lipids," *Poultry Sci.* 46: 438-444 (1967).
Miller et al., "Effect of Dietary Fat on Tissue Fat and Plasma Cholestrol Level in Broilers," *Poultry Sci.* 41: 970-974 (1962).
Miller et al., "Effect of Feeding and Withdrawal of Menhaden Oil on the w3 and w6 Fatty Acid Content of Broiler Tissues," *J. Food Sci.* 34: 136-141 (1969).
Miller et al., "Effect of Refined Menhaden Oils on the Flavor and Fatty Acid Composition of Broiler Flesh," J. Food Sci. 32: 342-345 (1967).
Miller, "Isolation and Pure Culture of Aquatic Phycomycetes by Membrane Filtration," *Mycologia* 59: 524-527 (1967).
Mokady et al., "Nutritional Evaluation of the Protein of Several Algae Species for Broilers," *Arch. Hydrobiol. Beih. Ergebn. Limmol.* 11: 89-97 (1978).
Mokady et al., "Protein Nutritive Value of Several Microalgae Species for Young Chickens and Rats," 655-660, *Algae Biomass*, Shelef and Soeder, eds., Elsevier/North-Holland Biomedical Press (1980).
Moore-Landecker, "Growth of Fungi in Culture," *Fundamentals of the Fungi* 280-307 (1982).
Moreton (ed.), "Physiology of Lipid Accumulated Yeasts," in *Single Cell Oil*, 1-32, John Wiley & sons, Inc., New York (1988).
Moss, "Biology and Phylogeny of the Labrinthulales and Thraustochytriales," 105-129, in *The Biology of Marine Fungi*, S.T. Moss ed., Cambridge University Press (1986).
Murty et al., "Influence of Graded Levels of Dietary Linoleic and Linolenic Acids on the Fatty Acid Composition of Hens' Eggs," *J. Nutrition* 75: 287-294 (1961).
"n-3 News Unsaturated Fatty Acids and Health," III(1): 1-4 (Mar. 1988).
Navarro et al., "Influence of Dietary Fish Meal on Egg Fatty Acid Composition," *J. Sci. Fd. Agric.* 23: 1287-1292 (1972).
Neudoerffer et al., "Effects of dietary fish oil on the composition and stability of turkey depot fat," *Br. J. Nutr.* 20: 581-594 (1966).
Nir, "Performance of Broilers Fed Diets Supplemented with 1.5% Soybean or Redfish Oil," *Poultry Sci. Suppl.* Abstract of Papers, 69(1): 99 (1990).
Nwokolo and Sim, "w-3 Fatty Acid Enrichment of Broiler and Layer Tissues, and Egg Yolk by Feeding Flax and Canola Seed Diets," *Poultry Sci.* 68(Suppl): 106, Abstract, 78th Ann. Poultry Sci. Assn. Mtg (1990).
Opstvedt et al., "Influence of Residual Lipids on the Nutritive Value of Fish Meal," *Acta Agri. Scand.* 20: 185-193 (1970).
Opstvedt, "Influence of Residual Lipids on Nutritive Value of Fish Meal," *Acta Agric. Scand.* 23: 217-224 (1973).
Opstvedt, "Influences of Residual Lipids on the Nutritive Value of Fish Meal," *Acta Agri. Scand.* 23: 200-208 (1973).
Orcutt and Patterson, "Sterol, Fatty Acid and Elemental Composition of Diatoms Grown in Chemically Defined Media," *Comp. Biochem. Physiol.* 50B: 579-83 (1975).
Perkins, "Phylogenetic Considerations of the Problematic Thraustochytriaceous-Labrinthulid-Dermocystidium Complex Based on Observations of Fine Structure," *Veroff. Inst. Meeresforsch. Bremerh. Suppl.* 5: 45-63 (1974).
Perkins, F. O. (1976) "Fine structure of lower marine and estuarine fungi." In: Recent Advances in marine Mycology, E. B. Gareth Jones (ed.), Elek Science, pp. 279-312.
Phetteplace and Watkins, "Dietary n-3 Fatty Acids Lowered Plasma Triacylglycerols in Male Broilers," *Poultry Sci.* 68(Supp. 1): 114 Abstract, 78th Ann. Poultry Sci. Assn. Mtg (1990).
Phetteplace et al., "Effects of Dietary n-6 and n-3 Fatty Acids on Lipid Metabolism in Two Genetic Lines of Broilers," *Poultry Sci.* 68(Suppl. 1): 114, Abstract, 78th Ann. Poultry Sci. Assn. Mtg (1990).
Pigott, "The Need to Improve Omega-3 Content of Cultured Fish," *World Aquaculture* 20:63-68 (1989).
Pirt "Aeration and Agitation Methods," in *Principles of Microbe and Cell Cultivation*, pp. 94-106, Blackwell Scientific Publications (1975).
Pohl et al., "Fatty Acids and Lipids of Marine Algae and the Control of Their Biosynthesis by Environmental Factors," 473-523, *Marine Algae in Pharmaceutical Science*, Hoppe et al. eds. (1979).
Porter "Phylogeneic considerations of the *Thraustochytriaceae* and *Labrinthulaceae*," *Veroff. Inst. Meeresforsch. Bremerh. Suppl.* 5: 19-44 (1974).

Porter, "Studies on the Physiology of Thraustochytriales . . . ," *Handbook of Protoctista*, Chapter 22, 388-398, Jones and Bartlett Publishers (1989).

Poyton, R., "The characteristization of *Hyallochlorella marina* gen. et sp. nov. a new colorless counterpart of Chlorella," *J. Gen. Microbiol.* 62: 171-188 (1970).

Provasoli et al. "Nutrition of the American Strain of *Gyrodinium eohnii" Archiv fur Mikrobiologie* 42: 196-203 (1962).

Radwan, "Sources of C20-Polyunsaturated Fatty Acids for Biotechnical Use," *Appl. Microbiol. Biotechnol.* 35: 421-430 (1991).

Raghukumar and Schaumann, "An epifuorescence microscopy method for direct detection and enumeration of the fungilike marine protists, the thraustochytrids," *Limnol. Oceanogr.* 38(1): 182-187 (1993).

Raghukumar et al., "Abundance of Thraustochytrid Fungi in the Arabian Sea," 31: 351-358, in *Estuarine—Coastal and Shelf Science* (1990).

Raghu-Kumar, S. "*Schizochytrium mangrovei* Sp. Nov., A Thraustochytrid From Mangroves in India," *Trans. Br. Mycol. Soc.* 90(4): 627-631 (1988 a).

Raghu-Kumar, S. "*Schizochytrium octosporum* Sp. Nov. and Other Thraustochytrids from the North Sea (Nosfjord, Norway)" *Trans. Br. Mycol. Soc.* 90(2): 273-278 (1988 b).

Ratledge "Microbial oils and fats: an assessment of their commercial potential," *Prog. Ind. Microbiol* 16: 119-206 (1982).

Ratledge, *Biotechnology of Oils and Fats*, 566-583 (1989).

Reid, G.K. , *Ecology of Inland Waters and Estuaries*, 294-295, Reinhold Publishing Corporation (1961).

Reiser, "The Syntheses and Interconversions of Polyunsaturated Fatty Acids by the Laying Hens" *J. Nutrition* 44: 159-175 (1951).

*ROMPP* regarding "anaerobic," 181 (1993).

*ROMPPS Chemielexikon 9*, Seiten 2669 and 2670, "Stichwort: Meerwasser zwei zustzliche Eingabenkopien eischliesslich Analagen" (1991).

Rouser et al., "Lipid Composition of Beef Brain, Beef Liver, and the Sea Anemone: Two Approaches to Quantitiative Fractionation of Complex Lipid Mixtures," *The Journal of the American Oil Chemists' Society* 40: 425-454 (1963).

Ryther, "Cultivation of Macroscopic Marine Algae," 79-88, Solar Energy Research Institute Aquatic Species Program Review. *Proc of the Mar. 1983 Principal Investigators Meeting*, SERI/CP/-231 1946 (1983).

Sargent, J. et al. "The lipids," in *Fish Nutrition*, Second Edition, J. Halver (ed.), Academic Press, 153-218 (1989).

Schlenk, "Urea Inclusion Compounds of Fatty Acids," *Prog. Chem. Fats and Other Lipids* 2:243-267 (1954).

Schneider, "Cultivation of Micro-organisms. Section 3.2: Fungi," 337-345, in *Marine Ecology*, vol. 3, Part 1. Cultivation, O. Kinne ed., Wiley and Sons (1976).

Schneider, "Zur Taxonomie, Verbreitung and Okologie einiger mariner Phycomyceten," *Aus dem Institut fur Meereskunde an der Universistat Kiel*, 316-327 (1969).

Schneider, J. "Ein neuer mariner Phycomycet as der. Kieler Bucht (*Thraustochytrium striatum* spc. nov.)," *Kieler Meeresforsch.* 23: 16-20 (1967).

Sell et al., "Fatty Acid Composition of Egg Yolk and Adipose Tissue as Influenced by Dietary Fat and Strain of Hen," 47: 1296-1302 (1968).

Seto et al., "Culture Conditions Affect Eicosapentaenoic Acid Content of *Chlorella minutissima" JAOCS* 61(5): 892-894 (1984).

Shimizu et al. "Fungal Mycelia as a Novel Source of Eicosapentaenoic Acid," *Biochemical and Biophysical Research Communications*, 150(1): 335-341 (Jan. 15, 1988).

Shimizu et al. "Production of Eicosapentaenoic Acid by Mortierella Fungi," *JAOCS*, 65(9): 1455-1459 (Sep. 13, 1988).

Shimizu et al., "Microbial Conversion of an Oil Containing alpha-Linolenic Acid to an Oil containing Eicosapentaenoic Acid," *JAOCS* 66(3): 342-347 (Mar. 1989).

Siegenthaler et al., "Phosphate Uptake in an Obligately Marine Fungus: A Specific Requirement for Sodium," *Science* 155: 93-94 (Jan. 6, 1967).

Silversand et al. "Improved High-performance liquid chromatographic method for the separation and quantification of lipid classes: application to fish lipids," *Journal of Chromatography B*. 703: 7-14 (1997).

Simopoulos et al. (eds.), *Health Effects of Polyunsaturated Fatty Acids in Seafoods*, Chaps. 2-5, 7 and 17, Academic Press (1986).

Simopoulos et al., "Purslane: a terrestrial source of w-3 fatty acid," *N. Engl. J. Med.* 315: 833 (1986).

Simopoulos, "Summary of the NATO advanced research workshop on dietary omega 3 and omega 6 fatty acids: biological effects and nutritional essentiality," *The Journal of Nutrition*, 119(4): 521-528 (Apr. 1989).

Sonnenborn and Kunau, "Purification and Properties of the Fatty Acid Synthetase Complex from the Marine Dinoflagellate, *Crypthecodinium cohnii," Biochimica et Biophysica Acta*. 712: 521-528 (1982).

Sorokin, "Dry Weight, Packed Cell Volume and Optical Density," 321-343, in *Handbook of Phycological Methods: Culture Methods and Growth Measurements*, J.R. Stein ed., Cambridge University Press) (1973).

Sparrow "Mastigomycotina (zoosporic fungi)," 61-73, in *The Fungi, An Advanced Treatise*, Ainsworth, Sparrow and Sussman (eds.), Academic Press, N.Y. (1973).

Sparrow, *Aquatic Phycomycetes*, 36-39, University of Michigan Press (1960).

Sparrow, F.K. "Biological Observations on the marine Fungi of Woods Hole Waters" *Bio. Bull.* 70: 236, 237, 259-263 (1936).

Stanbury et al., "Principles of Fermentation Technology," 121-123, 236-237, 242-243 (1984).

Stanbury et al., *Principles of Fermentation Technology*, Second Edition, pp. 215,222-224 (Feb. 19, 1999).

Hagemeister et al., "Biobusiness for Milchwissenschaft," *STN Database* AN 88: 13222 43(3):153, 155-158 (1988).

T. Long, "Caplus for WO 88-US2483," *STN Database* AN 89: 532569 (Jul. 20, 1988).

Ter Mulen, U. et al., "Metabolic Studies on the Antioxidant Ethooxyquin," *Journal of Animal Physiology, Animal Feed Information*, 43(3): 164-170 (1980).

Todorov, D., "Possibilities for Increasing the Biological Value of Alimentary Protein," *KHIGZDRAVFODAZ* 21(3): 291-297 (1978).

Tornabene, "Sterols, Aliphatic Hydrocarbons, and Fatty Acids of a Nonphotosynthetic Diatom, *Nitzschia alba*," *Lipids* 9(4): 279-284 (1974).

Tuttle et al., "An optimal Growth Medium for the Dinoflagellate *Crypthecodinium cohnii*," *Phycologia* 14: 1-8 (1975).

Ukeles, *Marine Ecology*, III(1): 367-466 (1976).

Ukeles, *Marine Ecology*, III(1): 447-451 (1976).

Ulken, (with partial English computer translation) *A. Veroff. Inst. Meeresforsch. Bremerha*. 9: 289-295 (1965).

Ulken, A. et al., "On the role of Phycomycates in the food web of different mangrove swamps with brackish waters and waters of high salinity," *European Marine Biology Symposium*, 1981, Abstract AN 81: 19970 (Sep. 29, 1990).

van der Werth, A. "Olgewinnung durch Extraktion" (including translation), 680-683, in *Chemie and Technologie der Fette und Fettprodukte*, Julius Springer, Wien (1936).

Van Winkle, "The effects of season, temperature, and salinity on the oxygen consumption of bivalve gill tissue," *Comp. Biochem. Physiol*. 26: 69-80 (1968).

Van Winkle, "Effect of environmental factors on byssal thread formation," *Marine Biology* 7: 143-148 (1970).

Vishniac, "Salt Requirements of Marine Phycomycetes," *Limnol. Oceanogr* 5: 362-365 (1960).

Vishniac, "Division of Mycology," 352-360, *Transactions of the New York Academy of Sciences* (1955).

Voet et al., *Biochemistry*, 2nd Edition, 279, John Wiley & Sons, Inc. (1995).

Vogel, H.U.v., *Chemiker-Kalender*, 1605, Springer Verlag, Berlin (1974).

VWR Catalog, 6 pages (2000/2001).

Wakelyn, "Regulatory Considerations for Extraction Solvents for Oilseeds and other nonpetroleum Oils" 49-51, in *Edible Oil Processing*, Sheffield Academic Press (2000).

Waldroup et al., "Fish Meal Studies. 1. Effects of Levels and Sources on Broiler Growth Rate and Feed Efficiency," *Poultry Sci.* 44: 1012-1016 (1965).
Walz et al., "Studies on Some Nutritive Effects of the Green Algae *Scenedesmus acutus* with Pigs and Broilers," 733-744, in *Algae Biomass*, Shelef and Soeder, eds., Elsevier/North-Holland Biomedical Press (1980).
Wassef, "Fungal Lipids," *Adv. Lipid Res.*15: 159-232, (1977).
Weete, "Fatty Acids," Chapter 3, pp. 49-95, 1980, in Lipid Biochemistry of Fungi and Other Organisms, (Plenum Press).
Wessinger "Production of Long-Chain-Polyunsaturated Fatty Acids by Selected Species," 74, Program and Abstracts of the 46th Annual Meeting of the Society for Industrial Microbiology (Aug. 13-18, 1989).
Wetzel, "Salinity of Inland Waters," *Limnology* 142-165 (1975).
Wheeler et al., "Fatty Acid Distribution in Egg Yolk as Influenced by Type and Level of Dietary Fat," *J. Nutrition* 69: 253-257 (1959).
Yamada et al., "Production of Arachidonic Acid and Eicosapentaenoic Acid by Microorganisms," *J. Am. Oil Chem. Soc.* 64:1254 (1987).
Yamada et al., "Production of Dihomo-.gamma.-Linolenic Acid, Arachidonic Acid and Eicosapentaenoic Acid by Filamentous Fungi," pp. 118-138, in *Industrial Application of Single Cell Oils*, Kyle et al., eds., American Oil Chemists' Society, Champaign, IL (1992).
Yannai et al., "The Safety of Several Algae Grown on Wastewater as a Feedstuff for Broilers," *Arch. Hydrobiol. Beih. Ergebn. Limnol.* 11: 139-149 (1978).
Yau et al., "Enrichment of Selected Fatty Acids in Broiler Tissues," Poultry Sci., 68(Suppl. 1): 162, Abstract, 78th Ann. Poultry Sci. Assn. Mtg. (1990).
Yazawa et al., "Production of Eicosapentaenoic Acid by Marine Bacteria," *J. Biochem.* 103: 5-7 (1988).
Yongmanitchai et al., "Growth of and Omega-3 Fatty Add Production by Phaeodactylum," *Applied and Environmental Microbiology*, 419-425 (1991).
Yongmanitchai et al., "Omega-3 Fatty Acids: Alternative Sources of Production," *Proc. Biochem* 117-125 (1989).
Yongmanitchai et al., "Screening of Algae for Potential Alternative Sources of Eicosapentaenoic Acid," *Phytochemistry* 30: 2963-2967 (1991).
*Zoosporic Fungi in Teaching & Research*, 7, 110-116, 128-129, 294-298 Fuller et al. (eds.) (1987).
Answering Brief by Defendants to Plaintiff's Motions to Strike Defense and to Dismiss Counterclaims in Civil Action No. 03-896, dated Dec. 29, 2003, 24 pages.
Appellants' Response and Reply Brief in U.S. Court of Appeals for the Federal Circuit Case No. 2008-1459,-1476, dated Jan. 5, 2009, 75 pages.
Comparative data on Total Omega-3 fatty acid production of different strains, Nov. 13, 2000, 1 page, document cited in opposition to European Patent No. EP 0512997.
Defendants' 3rd Supplemental Responses and Objections to Plaintiff's Interrogatories Nos. 3 and 4 in Civil Action No. 03-896-GMS dated Jan. 27, 2006, pp. 1-24.
Defendants' Responses and Objections to Plaintiff's Second Set of Interrogatories (No. 9) in Civil Action No. 03-896-GMS dated Jun. 17, 2005, pp. 1-5.
Defendants' Trial Brief (Exhibit 20) in Civil Action No. 03-896-GMS dated Aug. 14, 2006, pp. 1-16.
Defendants' 3d Supplemental Responses and Objections to Plaintiff's Interrogatories Nos. 3 and 4, Corrected Version, dated Jan. 30, 2006, at pp. 1-3, 24-28.
Defendants' Responses and Objections to Plaintiff's [Martek's] First Set of Interrogatories (Nos. 1-8), dated Mar. 29, 2005, at pp. 1-4, 6, 15-23.
Documents from File History for European Opposition of European Patent No. 0512997, dated between Jun. 15, 2009 to Jun. 25, 2009.
Documents from File History for European Opposition of European Patent No. 1251744, dated between Mar. 29, 2010 to Apr. 19, 2010.
Trial Brief of Plaintiff Martek Biosciences Corporation (Exhibit 19 of Pretrial Order) in Civil Action No. 03-896-GMS dated Aug. 14, 2006, pp. 1-16 (redacted).
Federal Circuit Decision in U.S. Court of Appeals for the Federal Circuit Case No. 2008-1459,-1476, decided Sep. 3, 2009, 36 pages.
File History for European Opposition of European Patent No. 0512997 May 6, 1998 to May 7, 2008.
File History for European Opposition of European Patent No. 0512997, Jun. 5, 1998 to Jun. 25, 2009.
File History for European Opposition of European Patent No. 0512997, Sep. 2, 2008 to Apr. 30, 2009.
File History for European Opposition of European Patent No. 0512997, Dec. 11, 1990 to May 6, 1998.
File History for European Opposition of European Patent No. 0669809, Feb. 2, 2010 to Feb. 12, 2010.
File History for European Opposition of European Patent No. 0669809, Mar. 3, 2004 to Feb. 12, 2010.
File History for European Opposition of European Patent No. 0669809, Sep. 17, 2008 to May 4, 2009.
File History for European Opposition of European Patent No. 0669809, Sep. 8, 2009 to Sep. 14, 2009.
Final Pretrial Order in Civil Action No. 03-896-GMS dated Aug. 14, 2006, pp. 1-6.
International Preliminary Examination Report for International (PCT) Patent Application No. PCT/US90/6375, mailed Dec. 5, 1995.
International Preliminary Examination Report for International (PCT) Patent Application No. PCT/US93/09679, mailed Mar. 20, 1995.
International Preliminary Examination Report for International (PCT) Patent Application No. PCT/US98/16892, mailed Dec. 9, 1999.
International Search Report for International (PCT) Patent Application No. PCT/US90/6375, mailed Feb. 26, 1991.
International Search Report for International (PCT) Patent Application No. PCT/US93/09679, mailed Jan. 19, 1994.
International Search Report for International (PCT) Patent Application No. PCT/US98/16892, mailed Nov. 17, 1998.
Joint Appendix, vol. I of II (pp. A1 to A7344), in U.S. Court of Appeals for the Federal Circuit Case No. 2008-1459,-1476, dated Jan. 29, 2009, 599 pages.
Joint Appendix, vol. II of II (pp. A7349 to A23247), in U.S. Court of Appeals for the Federal Circuit Case No. 2008-1459,-1476, dated Jan. 29, 2009, 600 pages.
Letter from John G. Day to Judge Sleet in Civil Action No. 1: 03-cv-00896-GMS, dated Dec. 3, 2009, 12 pages.
Letter from John G. Day to Judge Sleet in Civil Action No. 1: 03-cv-00896-GMS, dated Mar. 25, 2010, 4 pages.
Letter from Stephen J. MacKenzie to Judge Sleet in Civil Action No. 1: 03-cv-00896-GMS, dated Mar. 11, 2010, 29 pages.
Letter from Stephen J. MacKenzie to Judge Sleet in Civil Action No. 1: 03-cv-00896-GMS, dated Mar. 24, 2010, 18 pages.
Letter from Stephen J. MacKenzie to Judge Sleet in Civil Action No. 1: 03-cv-00896-GMS, dated Dec. 3, 2009, 79 pages.
Letter from Tiffany Geyer Lydon to Judge Sleet in Civil Action No. 1: 03-cv-00896-GMS, dated Mar. 24, 2010, 1 page.
Minutes of the Oral proceedings before the Examining Division on May 21, 1996 for European Patent Application No. 90916891.6, minutes mailed Jun. 10, 1996, 5 pages.
Motion for Summary Judgment Letter in Civil Action No. 03-896-GMS dated Mar. 14, 2006, pp. 1-3.
Complaint and Demand for Jury Trial, in Civil Action No. 03-896-GMS, filed Sep. 23, 2003.
Trial Transcript for *Martek v. Lonza*, Civil Action No. 03-896 (D. Del.), Oct. 13, 2006, at p. 645:17-25.
File History for European Opposition of European Patent No. 0512997, Jun. 25, 2009 to Sep. 29, 2010.
Motion for Leave to File an Amended Answer and Counterclaims to Martek's Fourth Amended Complaint Pursuant to Fed.R.Civ.P. 15(a)—filed by Food Ingredients Gmb, Lonza Ltd, Nutrinova Inc., Nutrinova Nutrition Specialties & Food Ingredients GmbH. (Attachments: # 1 Text of Proposed Order Tab 1, # 2 Tab 2—Amended Answer and Counterclaims, # 3 Tab 3—Blackline of Amended Answer and Counterclaim, # 4 Certificate of Service)(MacKenzie, Stephen) (Entered: Jun. 1, 2010), in Civil Action No. 1:03-CV-00896-GMS, 48 pages.

Opening Brief in Support Motion for Leave to File an Amended Answer and Counterclaims to Martek's Fourth Amended Complaint Pursuant to Fed.R.Civ.P. 15(a) Motion for Leave to File an Amended Answer and Counterclaims to Martek's Fourth Amended Complaint Pursuant to Fed.R.Civ.P. 15(a) filed by Food Ingredients Gmb, Lonza Ltd, Nutrinova Inc., Nutrinova Nutrition Specialties & Food Ingredients GmbH. Answering Brief/Response due date per Local Rules is Jun. 18, 2010) (Attachments: # 1 Certificate of Service) (MacKenzie, Stephen) (Entered: Jun. 1, 2010).

So Ordered, Motion for Leave to File an Amended Answer and Counterclaims to Martek's Fourth Amended Complaint Pursuant to Fed.R.Civ.P. 15(a) Motion for Leave to File an Amended Answer and Counterclaims to Martek's Fourth Amended Complaint Pursuant to Fed.R.Civ.P. 15(a) filed by Lonza Ltd, Nutrinova Nutrition Specialties & Food Ingredients GmbH, Nutrinova Inc., Food Ingredients Gmb. It Is Further Ordered that counsel file the Amended Answer and Counterclaims as a separate entry on the docket. Ordered by Chief Judge Gregory M. Sleet on Jun. 3, 2010. (asw) (Entered: Jun. 3, 2010), in Civil Action No. 1:03-CV-00896-GMS, 14 pages.

Answer to Complaint with Jury Demand (Answer to Counterclaims as to the '244 Patent) by Martek Biosciences Corporation.(Day, John) (Entered: Jun. 28, 2010), in Civil Action No. 1:03-CV-00896-GMS, 5 pages.

Motion to Stay Litigation Pending Reexamination of the Patent-In-Suit—filed by Martek Biosciences Corporation. (Attachments: # 1 Exhibit A , # 2 Rule 7.1.1. Certification) (Lydon, Tiffany) (Entered: Aug. 31, 2010), in Civil Action No. 1:03-CV-00896-GMS, 14 pages.

Response to Motion, Motion to Stay Litigation Pending Reexamination of the Patent-In-Suit filed by Nutrinova Inc. (Attachments: #1 Certificate of Service) (MacKenzie, Stephen) (Entered: Sep. 10, 2010), in Civil Action No. 1:03-CV-00896-GMS, 9 pages.

Reply Brief, Motion to Stay Litigation Pending Reexamination of the Patent-In-Suit filed by Martek Biosciences Corporation. (Lydon, Tiffany) (Entered: Sep. 20, 2010), in Civil Action No. 1:03-CV-00896-GMS, 9 pages.

Letter to The Honorable Gregory M. Sleet from John G. Day regarding developments in pending reexamination—Motion to Stay Litigation Pending Reexamination of the Patent-In-Suit. (Attachments: #1 Amendment and Response)(Day, John) (Entered: Oct. 6, 2010), in Civil Action No. 1:03-CV-00896-GMS, 75 pages.

Letter to the Honorable Gregory M. Sleet from Stephen J. MacKenzie regarding in response to Martek's counsel's Oct. 6, 2010 letter regarding reexamination—Letter (MacKenzie, Stephen) (Entered: Oct. 8, 2010), in Civil Action No. 1:03-CV-00896-GMS, 2 pages.

Motion to Dismiss—filed by Food Ingredients Gmb, Lonza, Ltd, Nutrinova Inc., Nutrinova Nutrition Specialties & Food Ingredients GmbH. (Attachments: #1 Certificate of Service) (MacKenzie, Stephen) (Entered: Oct. 18, 2010), in Civil Action No. 1:30-CV-00896-GMS, 6 pages.

Opening Brief in Support of Plaintiff's Motion to Strike Paragraph 26 of the Affirmative Defenses, Dismiss Paragraph 48 of Count I, and Dismiss Count III of the Counterclaims by Nutrinova Inc. and Nutrinova Nutrition Specialties & Food Ingredients GMBH in Civil Action No. 03-896-GMS, filed Dec. 15, 2003, 16 pages.

Opening Brief of Defendants-Appellants in U.S. Court of Appeals for the Federal Circuit Case No. 2008-1459,-1476, dated Sep. 9, 2008, 166 pages.

Plaintiff's Motion to Strike Paragraph 26 of the Affirmative Defenses, Dismiss Paragraph 48 of Count I, and Dismiss Count III of the Counterclaims by Nutrinova Inc. and Nutrinova Nutrition Specialties & Food Ingredients GMBH in Civil Action No. 03-896-GMS, filed Dec. 15, 2003, 5 pages.

Principal and Response Brief for Plaintiff-Cross Appellant Martek Biosciences Corporation, in U.S. Court of Appeals for the Federal Circuit Case No. 2008-1459,-1476, dated Nov. 21, 2008, 134 pages.

Reexam Litigation Search Conducted for Ex Parte Reexamination for U.S. Reexam Control No. 90/009,071, Apr. 30, 2008 and Oct. 14, 2009.

Reexam Litigation Search Conducted for Ex Parte Reexamination for U.S. Reexam Control No. 90/009,073, May 1, 2008 and Oct. 16, 2009.

Reexam Litigation Search Conducted for Ex Parte Reexamination for U.S. Reexam Control No. 90/009,122, May 19, 2008 and Sep. 29, 2009.

Reexam Litigation Search Conducted for Ex Parte Reexamination for U.S. Reexam Control No. 90/009,134, Jul. 2, 2008 and Sep. 24, 2009.

Reexam Litigation Search Conducted for Ex Parte Reexamination for U.S. Reexam Control No. 90/009,150, Jun. 3, 2008 and Dec. 9, 2009.

Reexam Litigation Search Conducted for Ex Parte Reexamination for U.S. Reexam Control No. 90/009,178, Jun. 19, 2008 and Oct. 15, 2009.

Reexam Litigation Search Conducted for Ex Parte Reexamination for U.S. Reexam Control No. 90/009,689, Mar. 25, 2010.

Reply Brief for Plaintiff-Cross Appellant Martek Biosciences Corporation in U.S. Court of Appeals for the Federal Circuit Case No. 2008-1459,-1476, dated Jan. 22, 2009, 41 pages.

Reply Brief in Support of Plaintiff's Motion to Strike Paragraph 26 of the Affirmative Defenses and Dismiss Paragraph 48 of Count I and Count III of the Counterclaims by Nutrinova Inc. and Nutrinova Nutrition Specialties & Food Ingredients GmbH in Civil Action No. 03-896-GMS, filed Jan. 9, 2004, 16 pages.

Report of Expected Testimony of Dr. Charles G. Riordan in Civil Action No. 03-896-GMS dated Apr. 28, 2006, pp. 1-6.

Report of Expected Testimony of Dr. Karsten Schaumann in Civil Action No. 03-896-GMS dated Apr. 21, 2006, pp. 1-4.

Report of Expected Testimony of Dr. Oliver Zeumer in Civil Action No. 03-896-GMS dated Mar. 3, 2006, pp. 1-4.

Report of Expected Testimony of Dr. Owen Ward in Civil Action No. 03-896-GMS dated Apr. 28, 2006, pp. 1-15.

Report of Expected Testimony of Dr. Ric R. Grummer in Civil Action No. 03-896-GMS dated Mar. 6, 2006, pp. 1-13.

Report of Expected Testimony of Robert E. Tatnall in Civil Action No. 03-896-GMS dated Apr. 28, 2006, pp. 1-7.

Report of Expected Testimony of Thomas Veach Long, II, Ph.D. in Civil Action No. 03-896-GMS dated Apr. 28, 2006, pp. 1-11.

Transcript for *Martek* v. *Lonza* Teleconference Civil Action No. 03-896 (D. Del.), Mar. 15, 2009.

Written Opinion for International (PCT) Patent Application No. PCT/US90/6375, mailed Nov. 1, 1991.

Written Opinion for International (PCT) Patent Application No. PCT/US93/09679, mailed Aug. 31, 1994.

Written Opinion for International (PCT) Patent Application No. PCT/US98/16892, mailed May 27, 1999.

Goldstein, S. and Belsky, M. "Axenic Culture Studies of a New Marine Phycomycete Possessing an Unusual Type of Asexual Reproduction" (1964), Am. J. Bot. 51(1): 72-78.

"Joint Discovery Plan" in Civil Action No. 1: 03-cv-00896-GMS, filed Feb. 1, 2010, pp. 1-7.

"Martek Receives Favorable Ruling in Europe for DHA Food Patent," News Release, Source: Martek Biosciences Corporation, May 12, 2005, 1 page.

"Minute Entry for proceedings held before Judge Gregory M. Sleet—Telephone Conference Re: Status held on Dec. 4, 2009" in Civil Action No. 1: 03-cv-00896-GMS, entered Dec. 4, 2009, pp. 1-2.

"Minute Entry for proceedings held before Judge Gregory M. Sleet—Telephone Conference Re: Status/Discovery held on Mar. 15, 2010" in Civil Action No. 1: 03-cv-00896-GMS, entered Mar. 15, 2010, pp. 1-2.

"Notice of Service" in Civil Action No. 1: 03-cv-00896-GMS, filed Apr. 6, 2010, pp. 1-3.

"Scheduling Order [Proposed]" in Civil Action No. 1: 03-cv-00896-GMS, filed Mar. 24, 2010, pp. 1-5.

Stipulation Amending Certain Discovery Deadlines by Lonza Ltd, Martek Biosciences Corporation, Nutrinova Inc., Nutrinova Nutrition Specialties & Food Ingredients GmbH. (Day, John) (Entered: Oct. 22, 2010), in Civil Action No. 1:03-CV-00896-GMS, 3 pages.

So Ordered, Stipulation filed by Lonza Ltd, Nutrinova Nutrition Specialties & Food Ingredients GmbH, Martek Biosciences Corporation, Nutrinova Inc. Signed by Chief Judge Gregory M. Sleet on Oct. 26, 2010. (asw) (Entered: Oct. 26, 2010), in Civil Action No. 1:03-CV-00896-GMS, 3 pages.

Answering Brief in Opposition Motion to Dismiss filed by Martek Biosciences Corporation. (Day, John) (Entered: Nov. 1, 2010), in Civil Action No. 1:03-CV-00896-GMS, 6 pages.

Reply to Response to Motion to Dismiss filed by Lonza Ltd, Nutrinova Inc., Nutrinova Nutrition Specialties & Food Ingredients GmbH. (MacKenzie, Stephen) (Entered: Nov. 8, 2010), in Civil Action No. 1:03-CV-00896-GMS, 7 pages.

Motion for Extension of Time to Amend Certain Discovery Deadlines—filed by Food Ingredients Gmb, Lonza Ltd, Nutrinova Inc., Nutrinova Nutrition Specialties & Food Ingredients GmbH. (MacKenzie, Stephen) (Entered: Dec. 13, 2010), in Civil Action No. 1:03-CV-00896-GMS, 3 pages.

English language abstract of Schneider, "Zur Taxonomie, Verbreitung und Okologie einiger mariner Phycomyceten," Aus dem Institut fur Meereskunde an der Universistat Kiel, 1969, pp. 316-327.

Defendant-Appellant Lonza, Ltd.'s Combined Petition for Rehearing and Rehearing En Banc of the Federal Circuit Decision of Sep. 3, 2009 in U.S. Court of Appeals for the Federal Circuit Case No. 2008-1459,-1476, executed Oct. 5, 2009, 58 pages.

Proposed Order (Stipulated Order Permitting Amendment of the Complaint to Join an Additional Defendant) by Martek Biosciences Corporation, Nutrinova Inc., Nutrinova Nutrition Specialities & Food Ingredients GmbH. (Attachments: #1 Fourth Amended Complaint, #2 Exhibit A to Fourth Amended Complaint, #3 Exhibit B (part I) to Fourth Amended Complaint, #4 Exhibit B (part II) to Fourth Amended Complaint, #5 Exhibit C to Fourth Amended Complaint, #6 Exhibit D to Fourth Amended Complaint) (Day, John) (Entered: Apr. 20, 2006)) (Entered: Jun. 4, 2010), in Civil Action No. 1:03-CV-00896-GMS, 103 pages.

So Ordered, Proposed Order, filed by Martek Biosciences Corporation, Nutrinova Inc., Nutrinova Nutrition Specialties & Food Ingredients GmbH. Signed by Judge Gregory M. Sleet on Apr. 21, 2006. (asw) (Entered Apr. 21, 2006), in Civil Action No. 1:03-CV-00896-GMS, 3 pages.

Objections by Food Ingredients Gmb, Lonza Ltd, Nutrinova Inc., Nutrinova Nutrition Specialties & Food Ingredients GmbH So Ordered, Proposed Order, Amended Answer and Counterclaims to Martek's Fourth Amended Complaint as to the '244 Patent (Attachment #1: Certificate of Service)(MacKenzie, Stephen) (Entered: Jun. 4, 2010), in Civil Action No. 1:03-CV-00896-GMS, 12 pages.

Bowles, et al.; "Long chain n—3 polyunsaturated fatty acid production by members of the marine protistan group of the thraustochytrids: screening of isolates and optimization of docosahexaenoic acid production"; Journal of Biotechnology; 1999; vol. 70, No. 1-3; pp. 193-202.

Singh, et al.; "Docosahexaenoic acid (DHA) production by *Thraustochytrium* sp. ATCC 20892"; World Journal of Microbiology & Biotechnology; 1996; vol. 12, No. 1; pp. 76-81.

Iida, et al.; "Improvement of Docosahexaenoic Acid Production in a Culture of *Thraustochytrium auream* by Medium Optimization"; Journal of Fermentation and Bioengineering; 1996; vol. 81, No. 1; pp. 76-78.

Li and Ward; "Production of docosahexaenoic acid by *Thraustochytrium roseum*"; Journal of Industrial Microbiology; 1994; vol. 13, No. 4; pp. 238-241.

Meesters, et al.; "High-cell-density cultivation of the lipid accumulating yeast *Cryptococcus curvatus* using glycerol as a carbon source"; Appl. Microbiol. Biotechnol.; 1996; vol. 45; pp. 575-579.

Riesenberg and Guthke; "High-cell-density cultivation of microorganisms"; Appl. Microbiol. Biotechnol.; 1999; vol. 51; pp. 422-430.

"Technology for Antibiotic Production"; edited by East Chemical Industry and Shenyang Pharmaceutical Institute; May 1982; Chemical Industry Press, 5 pages (in Chinese).

* cited by examiner

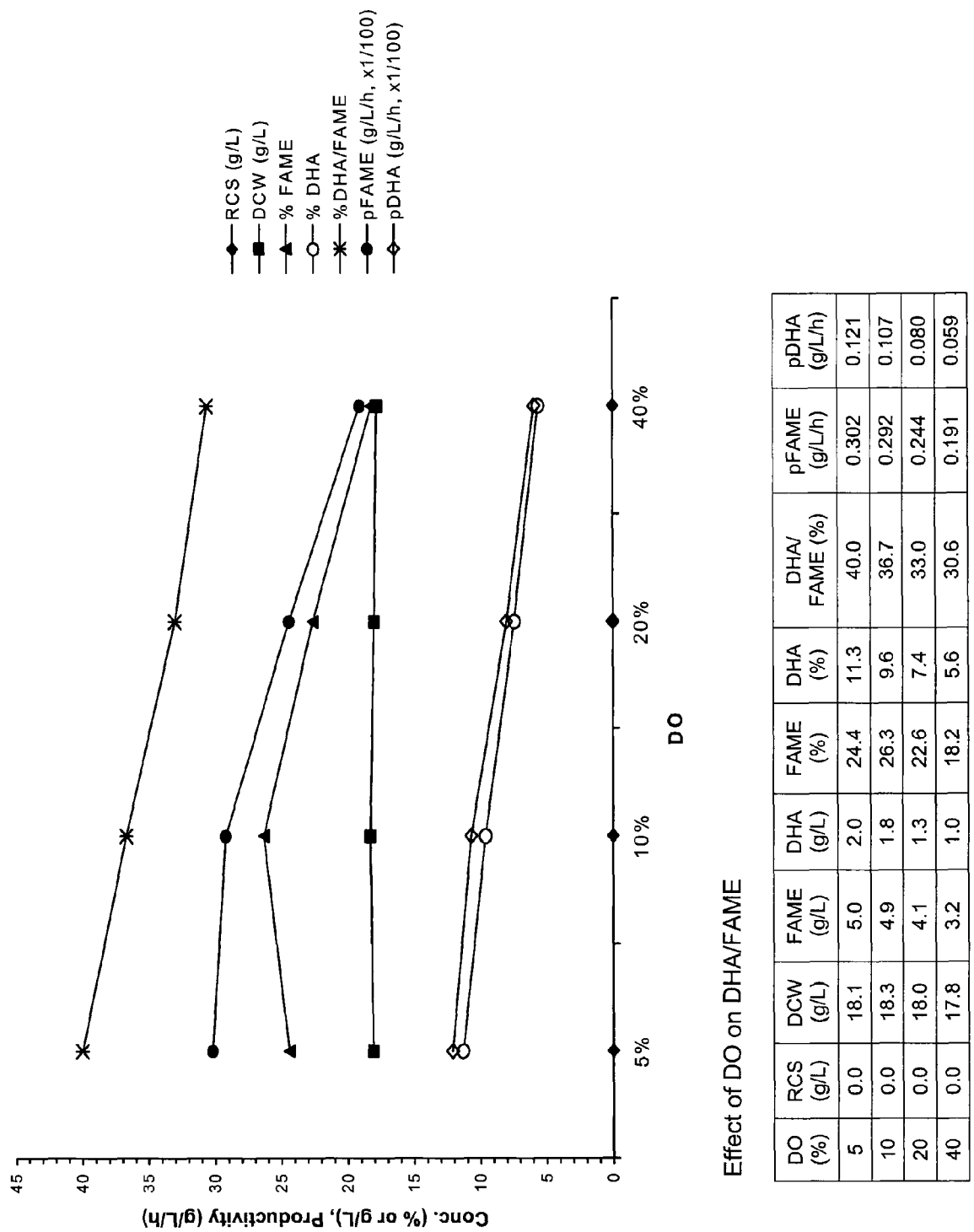

ENHANCED PRODUCTION OF LIPIDS CONTAINING POLYENOIC FATTY ACID BY VERY HIGH DENSITY CULTURES OF EUKARYOTIC MICROBES IN FERMENTORS

CROSS REFERENCE TO RELATED APPLICATIONS

The present application is a continuation of U.S. patent application Ser. No. 11/352,421, filed Feb. 10, 2006, which is a continuation of U.S. patent application Ser. No. 10/371,394, filed Feb. 21, 2003, now abandoned, which is a continuation of U.S. patent application Ser. No. 09/771,352, filed Jan. 26, 2001, now U.S. Pat. No. 6,607,900, which claims the benefit of priority under 35 U.S.C. §119(e) from Provisional Patent Application Ser. No. 60/178,588, filed on Jan. 28, 2000. Each of the foregoing applications is incorporated herein by reference in its entirety.

FIELD OF THE INVENTION

The present invention is directed to a novel process for growing microorganisms and recovering microbial lipids. In particular, the present invention is directed to producing microbial polyunsaturated lipids.

BACKGROUND OF THE INVENTION

Production of polyenoic fatty acids (fatty acids containing 2 or more unsaturated carbon-carbon bonds) in eukaryotic microorganisms is generally known to require the presence of molecular oxygen (i.e., aerobic conditions). This is because it is believed that the cis double bond formed in the fatty acids of all non-parasitic eukaryotic microorganisms involves a direct oxygen-dependent desaturation reaction (oxidative microbial desaturase systems). Other eukaryotic microbial lipids that are known to require molecular oxygen include fungal and plant sterols, oxycarotenoids (i.e., xanthophyls), ubiquinones, and compounds made from any of these lipids (i.e., secondary metabolites).

Eukaryotic microbes (such as algae; fungi, including yeast; and protists) have been demonstrated to be good producers of polyenoic fatty acids in fermentors. However, very high density cultivation (greater than about 100 g/L microbial biomass, especially at commercial scale) can lead to decreased polyenoic fatty acid contents and hence decreased polyenoic fatty acid productivity. This may be due in part to several factors including the difficulty of maintaining high dissolved oxygen levels due to the high oxygen demand developed by the high concentration of microbes in the fermentation broth. Methods to maintain higher dissolved oxygen level include increasing the aeration rate and/or using pure oxygen instead of air for aeration and/or increasing the agitation rate in the fermentor. These solutions generally increase the cost of lipid production and can cause additional problems. For example, increased aeration can easily lead to severe foaming problems in the fermentor at high cell densities and increased mixing can lead to microbial cell breakage due to increased shear forces in the fermentation broth (this causes the lipids to be released in the fermentation broth where they can become oxidized and/or degraded by enzymes). Microbial cell breakage is an increased problem in cells that have undergone nitrogen limitation or depletion to induce lipid formation, resulting in weaker cell walls.

As a result, when lipid producing eukaryotic microbes are grown at very high cell concentrations, their lipids generally contain only very small amounts of polyenoic fatty acids. For example, the yeast *Lipomyces starkeyi* has been grown to a density of 153 g/L with resulting lipid concentration of 83 g/L in 140 hours using alcohol as a carbon source. Yet the polyenoic fatty acid content of the yeast at concentration greater than 100 g/L averaged only 4.2% of total fatty acids (dropping from a high of 11.5% of total fatty acid at a cell density of 20-30 g/L). Yamauchi et al., *J. Ferment. Technol.*, 1983, 61, 275-280. This results in a polyenoic fatty acid concentration of only about 3.5 g/L and a polyenoic fatty acid productivity of only about 0.025 g/L/hr. Additionally, the only polyenoic fatty acid reported in the yeast lipids was C18:2.

Another yeast, *Rhodotorula glutinus*, has been demonstrated to have a lipid productivity of about 0.49 g/L/hr, but also a low overall polyenoic fatty acid content in its lipids (15.8% of total fatty acids, 14.7% C18:2 and 1.2% C18:3) resulting in a polyenoic fatty acid productivity in fed-batch culture of only about 0.047 g/L/hr and 0.077 g/L/hr in continuous culture.

Present inventors have previously demonstrated that certain marine microalgae in the order Thraustochytriales can be excellent producers of polyenoic fatty acids in fermentors, especially when grown at low salinity levels and especially at very low chloride levels. Others have described Thraustochytrids which exhibit a polyenoic fatty acid (DHA, C22:6n-3; and DPA, C22:5n-6) productivity of about 0.158 g/L/hr, when grown to cell density of 59 g/L/hr in 120 hours. However, this productivity was only achieved at a salinity of about 50% seawater, a concentration that would cause serious corrosion in conventional stainless steel fermentors.

Costs of producing microbial lipids containing polyenoic fatty acids, and especially the highly unsaturated fatty acids, such as C18:4n-3, C20:4n-6, C20:5n3, C22:5n-3, C22:5n-6 and C22:6n-3, have remained high in part due to the limited densities to which the high polyenoic fatty acid containing eukaryotic microbes have been grown and the limited oxygen availability both at these high cell concentrations and the higher temperatures needed to achieve high productivity.

Therefore, there is a need for a process for growing microorganisms at high concentration which still facilitates increased production of lipids containing polyenoic fatty acids.

SUMMARY OF THE INVENTION

The present invention provides a process for growing eukaryotic microorganisms which are capable of producing at least about 20% of their biomass as lipids and a method for producing the lipids. Preferably the lipids contain one or more polyenoic fatty acids. The process comprises adding to a fermentation medium comprising eukaryotic microorganisms a carbon source, preferably a non-alcoholic carbon source, and a nitrogen source. Preferably, the carbon source and the nitrogen source are added at a rate sufficient to increase the biomass density of the fermentation medium to at least about 100 g/L.

In one aspect of the present invention, the fermentation condition comprises a biomass density increasing stage and a lipid production stage, wherein the biomass density increasing stage comprises adding the carbon source and the nitrogen source, and the lipid production stage comprises adding the carbon source without adding the nitrogen source to induce nitrogen limiting conditions which induces lipid production.

In another aspect of the present invention, the amount of dissolved oxygen present in the fermentation medium during the lipid production stage is lower than the amount of dissolved oxygen present in the fermentation medium during the biomass density increasing stage.

In yet another aspect of the present invention, microorganisms are selected from the group consisting of algae, fungi, protists, and mixtures thereof, wherein the microorganisms are capable of producing polyenoic fatty acids or other lipids which requires molecular oxygen for their synthesis. A particularly useful microorganisms of the present invention are eukaryotic microorganisms which are capable of producing lipids at a fermentation medium oxygen level of about less than 3% of saturation.

In still another aspect of the present invention, microorganisms are grown in a fed-batch process. Moreover, Yet still another aspect of the present invention provides maintaining an oxygen level of less than about 3% of saturation in the fermentation medium during second half of the fermentation process.

Another embodiment of the present invention provides a process for producing eukaryotic microbial lipids comprising:
(a) growing eukaryotic microorganisms in a fermentation medium to increase the biomass density of said fermentation medium to at least about 100 g/L;
(b) providing a fermentation condition sufficient to allow said microorganisms to produce said lipids; and
(c) recovering said lipids,
wherein greater than about 15% of said lipids are polyunsaturated lipids.

Another aspect of the present invention provides a lipid recovery step which comprises:
(d) removing water from said fermentation medium to provide dry microorganisms; and
(e) isolating said lipids from said dry microorganisms.

Preferably, the water removal step comprises contacting the fermentation medium directly on a drum-dryer without prior centrifugation.

BRIEF DESCRIPTION OF THE DRAWINGS

FIG. 1 is a table and a plot of various lipid production parameters of a microorganism versus the amount of dissolved oxygen level in a fermentation medium.

DETAILED DESCRIPTION OF THE INVENTION

The present invention provides a process for growing microorganisms, such as, for example, fungi (including yeast), algae, and protists. Preferably, microorganisms are selected from the group consisting of algae, protists and mixtures thereof. More preferably, microorganisms are algae. Moreover, the process of the present invention can be used to produce a variety of lipid compounds, in particular unsaturated lipids, preferably polyunsaturated lipids (i.e., lipids containing at least 2 unsaturated carbon-carbon bonds, e.g., double bonds), and more preferably highly unsaturated lipids (i.e., lipids containing 4 or more unsaturated carbon-carbon bonds) such as omega-3 and/or omega-6 polyunsaturated fatty acids, including docosahexaenoic acid (i.e., DHA); and other naturally occurring unsaturated, polyunsaturated and highly unsaturated compounds. As used herein, the term "lipid" includes phospholipids; free fatty acids; esters of fatty acids; triacylglycerols; sterols and sterol esters; carotenoids; xanthophyls (e.g., oxycarotenoids); hydrocarbons; and other lipids known to one of ordinary skill in the art.

More particularly, processes of the present invention are useful in producing eukaryotic microbial polyenoic fatty acids, carotenoids, fungal sterols, phytosterols, xanthophyls, ubiquinones, other compounds which require oxygen for producing unsaturated carbon-carbon bonds (i.e., aerobic conditions), and secondary metabolites thereof. Specifically, processes of the present invention are useful in growing microorganisms which produce polyenoic fatty acid(s) and for producing microbial polyenoic fatty acid(s).

While processes of the present invention can be used to grow a wide variety of microorganisms and to obtain polyunsaturated lipid containing compounds produced by the same, for the sake of brevity, convenience and illustration, this detailed description of the invention will discuss processes for growing microorganisms which are capable of producing lipids comprising omega-3 and/or omega-6 polyunsaturated fatty acids, in particular microorganisms which are capable of producing DHA. More particularly, preferred embodiments of the present invention will be discussed with reference to a process for growing marine microorganisms, in particular algae, such as Thraustochytrids of the order Thraustochytriales, more specifically Thraustochytriales of the genus *Thraustochytrium* and *Schizochytrium*, including Thraustochytriales which are disclosed in commonly assigned U.S. Pat. Nos. 5,340,594 and 5,340,742, both issued to Barclay, all of which are incorporated herein by reference in their entirety. It is to be understood, however, that the invention as a whole is not intended to be so limited, and that one skilled in the art will recognize that the concept of the present invention will be applicable to other microorganisms producing a variety of other compounds, including other lipid compositions, in accordance with the techniques discussed herein.

Assuming a relatively constant production rate of lipids by an algae, it is readily apparent that the higher biomass density will lead to a higher total amount of lipids being produced per volume. Current conventional fermentation processes for growing algae yield a biomass density of from about 50 to about 80 g/L or less. The present inventors have found that by using processes of the present invention, a significantly higher biomass density than currently known biomass density can be achieved. Preferably, processes of the present invention produces biomass density of at least about 100 g/L, more preferably at least about 130 g/L, still more preferably at least about 150 g/L, yet still more preferably at least about 170 g/L, and most preferably greater than about 200 g/L. Thus, with such a high biomass density, even if the lipids production rate of algae is decreased slightly, the overall lipids production rate per volume is significantly higher than currently known processes.

Processes of the present invention for growing microorganisms of the order Thraustochytriales include adding a source of carbon and a source of nitrogen to a fermentation medium comprising the microorganisms at a rate sufficient to increase the biomass density of the fermentation medium to those described above. This fermentation process, where a substrate (e.g., a carbon source and a nitrogen source) is added in increments, is generally referred to as a fed-batch fermentation process. It has been found that when the substrate is added to a batch fermentation process the large amount of carbon source present (e.g., about 200 g/L or more per 60 g/L of biomass density) had a detrimental effect on the microorganisms. Without being bound by any theory, it is believed that such a high amount of carbon source causes detrimental effects, including osmotic stress, for microorganisms and inhibits initial productivity of microorganisms. Processes of the present invention avoid this undesired detrimental effect while providing a sufficient amount of the substrate to achieve the above described biomass density of the microorganisms.

Processes of the present invention for growing microorganisms can include a biomass density increasing stage. In the biomass density increasing stage, the primary objective of the fermentation process is to increase the biomass density in the fermentation medium to obtain the biomass density described above. The rate of carbon source addition is typically maintained at a particular level or range which does not cause a significant detrimental effect on productivity of microorganisms. An appropriate range of the amount of carbon source needed for a particular microorganism during a fermentation process is well known to one of ordinary skill in the art. Preferably, a carbon source of the present invention is a non-alcoholic carbon source, i.e., carbon source that does not contain alcohol. As used herein, an "alcohol" refers to a compound having 4 or less carbon atoms with one hydroxy group, e.g., methanol, ethanol and isopropanol. More preferably, a carbon source of the present invention is a carbohydrate, including, but not limited to, fructose, glucose, sucrose, molasses, and starch. Other suitable simple and complex carbon sources and nitrogen sources are disclosed in the above-referenced patents. Typically, however, a carbohydrate, preferably corn syrup, is used as the primary carbon source.

A particularly preferred nitrogen source is inorganic ammonium salt, more preferably ammonium salts of sulfate, hydroxide, and most preferably ammonium hydroxide.

When ammonium is used as a nitrogen source, the fermentation medium becomes acidic if it is not controlled by base addition or buffers. When ammonium hydroxide is used as the primary nitrogen source, it can also be used to provide a pH control. The microorganisms of the order Thraustochytriales, in particular Thraustochytriales of the genus *Thraustochytrium* and *Schizochytrium*, will grow over a wide pH range, e.g., from about pH 5 to about pH 11. A proper pH range for fermentation of a particular microorganism is within the knowledge of one skilled in the art.

Processes of the present invention for growing microorganisms can also include a production stage. In this stage, the primary use of the substrate by the microorganisms is not increasing the biomass density but rather using the substrate to produce lipids. It should be appreciated that lipids are also produced by the microorganisms during the biomass density increasing stage; however, as stated above, the primary goal in the biomass density increasing stage is to increase the biomass density. Typically, during the production stage the addition of the nitrogen substrate is reduced or preferably stopped.

It was previously generally believed that the presence of dissolved oxygen in the fermentation medium is crucial in the production of polyunsaturated compounds by eukaryotic microorganisms including omega-3 and/or omega-6 polyunsaturated fatty acids. Thus, a relatively large amount of dissolved oxygen in the fermentation medium was generally believed to be preferred. Surprisingly and unexpectedly, however, the present inventors have found that the production rate of lipids is increased dramatically when the dissolved oxygen level during the production stage is reduced. Thus, while the dissolved oxygen level in the fermentation medium during the biomass density increasing stage is at least about 8% of saturation, and preferably at least about 4% of saturation, during the production stage the dissolved oxygen level in the fermentation medium is reduced to about 3% of saturation or less, preferably about 1% of saturation or less, and more preferably about 0% of saturation. In one particular embodiment of the present invention, the amount of dissolved oxygen level in the fermentation medium is varied during the fermentation process. For example, for a fermentation process with total fermentation time of from about 90 hours to about 100 hours, the dissolved oxygen level in the fermentation medium is maintained at about 8% during the first 24 hours, about 4% from about $24^{th}$ hour to about $40^{th}$ hour, and about 0.5% or less from about $40^{th}$ hour to the end of the fermentation process.

The amount of dissolved oxygen present in the fermentation medium can be controlled by controlling the amount of oxygen in the head-space of the fermentor, or preferably by controlling the speed at which the fermentation medium is agitated (or stirred). For example, a high agitation (or stirring) rate results in a relatively higher amount of dissolved oxygen in the fermentation medium than a low agitation rate. For example, in a fermentor of about 14,000 gallon capacity the agitation rate is set at from about 50 rpm to about 70 rpm during the first 12 hours, from about 55 rpm to about 80 rpm during about 121 hour to about $18^{th}$ hour and from about 70 rpm to about 90 rpm from about $18^{th}$ hour to the end of the fermentation process to achieve the dissolved oxygen level discussed above for a total fermentation process time of from about 90 hours to about 100 hours. A particular range of agitation speeds needed to achieve a particular amount of dissolved oxygen in the fermentation medium can be readily determined by one of ordinary skill in the art.

A preferred temperature for processes of the present invention is at least about 20° C., more preferably at least about 25° C., and most preferably at least about 30° C. It should be appreciated that cold water can retain a higher amount of dissolved oxygen than warm water. Thus, a higher fermentation medium temperature has additional benefit of reducing the amount of dissolved oxygen, which is particularly desired as described above.

Certain microorganisms may require a certain amount of saline minerals in the fermentation medium. These saline minerals, especially chloride ions, can cause corrosion of the fermentor and other downstream processing equipment. To prevent or reduce these undesired effects due to a relatively large amount of chloride ions present in the fermentation medium, processes of the present invention can also include using non-chloride containing sodium salts, preferably sodium sulfate, in the fermentation medium as a source of saline (i.e., sodium). More particularly, a significant portion of the sodium requirements of the fermentation are supplied as non-chloride containing sodium salts. For example, less than about 75% of the sodium in the fermentation medium is supplied as sodium chloride, more preferably less than about 50% and more preferably less than about 25%. The microorganisms of the present invention can be grown at chloride concentrations of less than about 3 g/L, more preferably less than about 500 mg/L, more preferably less than about 250 mg/L and more preferably between about 60 mg/L and about 120 mg/L.

Non-chloride containing sodium salts can include soda ash (a mixture of sodium carbonate and sodium oxide), sodium carbonate, sodium bicarbonate, sodium sulfate and mixtures thereof, and preferably include sodium sulfate. Soda ash, sodium carbonate and sodium bicarbonate tend to increase the pH of the fermentation medium, thus requiring control steps to maintain the proper pH of the medium. The concentration of sodium sulfate is effective to meet the salinity requirements of the microorganisms, preferably the sodium concentration is (expressed as g/L of Na) at least about 1 g/L, more preferably in the range of from about 1 g/L to about 50 g/L and more preferably in the range of from about 2.0 g/L to about 25 g/L.

Various fermentation parameters for inoculating, growing and recovering microorganisms are discussed in detail in U.S.

Pat. No. 5,130,242, which is incorporated herein by reference in its entirety. Any currently known isolation methods can be used to isolate microorganisms from the fermentation medium, including centrifugation, filtration, decantation, and solvent evaporation. It has been found by the present inventors that because of such a high biomass density resulting from processes of the present invention, when a centrifuge is used to recover the microorganisms it is preferred to dilute the fermentation medium by adding water, which reduces the biomass density, thereby allowing more effective separation of microorganisms from the fermentation medium.

Preferably, the microorganisms are recovered in a dry form from the fermentation medium by evaporating water from the fermentation medium, for example, by contacting the fermentation medium directly (i.e., without pre-concentration, for example, by centrifugation) with a dryer such as a drum-dryer apparatus, i.e., a direct drum-dryer recovery process. When using the direct drum-dryer recovery process to isolate microorganisms, typically a steam heated drum-dryer is employed. In addition when using the direct drum-dryer recovery process, the biomass density of the fermentation medium is preferably at least about 130 g/L, more preferably at least about 150 g/L, and most preferably at least about 180 g/L. This high biomass density is generally desired for the direct drum-dryer recovery process because at a lower biomass density, the fermentation medium comprises a sufficient amount of water to cool the drum significantly, thus resulting in incomplete drying of microorganisms. Other methods of drying cells, including spray-drying, are well known to one of ordinary skill in the art.

Processes of the present invention provide a lipid production rate of at least about 0.5 g/L/hr, preferably at least about 0.7 g/L/hr, more preferably at least about 0.9 g/L/hr, and most preferably at least about 1.0 g/L/hr. Moreover, lipids produced by processes of the present invention contain polyunsaturated lipids in the amount greater than about 15%, preferably greater than about 20%, more preferably greater than about 25%, still more preferably greater than about 30%, and most preferably greater than about 35%. Lipids can be recovered from either dried microorganisms or from the microorganisms in the fermentation medium. Generally, at least about 20% of the lipids produced by the microorganisms in the processes of the present invention are omega-3 and/or omega-6 polyunsaturated fatty acids, preferably at least about 30% of the lipids are omega-3 and/or omega-6 polyunsaturated fatty acids, more preferably at least about 40% of the lipids are omega-3 and/or omega-6 polyunsaturated fatty acids, and most preferably at least about 50% of the lipids are omega-3 and/or omega-6 polyunsaturated fatty acids. Alternatively, processes of the present invention provides a DHA production rate of at least about 0.2 g of DHA/L/hr, preferably at least about 0.3 g of DHA/L/hr, more preferably at least about 0.4 g of DHA/L/hr, and most preferably at least about 0.5 g of DHA/L/hr. Still alternatively, at least about 25% of the lipid is DHA (based on total fatty acid methyl ester), preferably at least about 30%, more preferably at least about 35%, and most preferably at least about 40%.

Microorganisms, lipids extracted therefrom, the biomass remaining after lipid extraction or combinations thereof can be used directly as a food ingredient, such as an ingredient in beverages, sauces, dairy based foods (such as milk, yogurt, cheese and ice-cream) and baked goods; nutritional supplement (in capsule or tablet forms); feed or feed supplement for any animal whose meat or products are consumed by humans; food supplement, including baby food and infant formula; and pharmaceuticals (in direct or adjunct therapy application). The term "animal" means any organism belonging to the kingdom Animalia and includes, without limitation, any animal from which poultry meat, seafood, beef, pork or lamb is derived. Seafood is derived from, without limitation, fish, shrimp and shellfish. The term "products" includes any product other than meat derived from such animals, including, without limitation, eggs, milk or other products. When fed to such animals, polyunsaturated lipids can be incorporated into the flesh, milk, eggs or other products of such animals to increase their content of these lipids.

Additional objects, advantages, and novel features of this invention will become apparent to those skilled in the art upon examination of the following examples thereof, which are not intended to be limiting.

EXAMPLES

The strain of *Schizochytrium* used in these examples produces two primary polyenoic acids, DHAn-3 and DPAn-6 in the ratio of generally about 3:1, and small amounts of other polyenoic acids, such as EPA and C20:3, under a wide variety of fermentation conditions. Thus, while following examples only list the amount of DHA, one can readily calculate the amount of DPA produced by using the above disclosed ratio.

Example 1

This example illustrates the affect of oxygen content in a fermentation medium on lipid productivity.

Fermentation results of *Schizochytrium* at various levels of dissolved oxygen content were measured. The results are shown in FIG. 1, where RCS is residual concentration of sugar, and DCW is dry-cell weight.

Example 2

This example illustrates the reproducibility of processes of the present invention.

Microorganisms were produced using fermentors with a nominal working volume of 1,200 gallons. The resulting fermentation broth was concentrated and microorganisms were dried using a drum-dryer. Lipids from aliquots of the resulting microorganisms were extracted and purified to produce a refined, bleached, and deodorized oil. Approximately 3,000 ppm of d-1-α-tocopheryl acetate was added for nutritional supplementation purposes prior to analysis of the lipid.

Nine fermentations of *Schizochytrium* were run and the results are shown in Table 1. The dissolved oxygen level was about 8% during the first 24 hours and about 4% thereafter.

TABLE 1

Fed-batch fermentation results for the production of DHA.

| Entry | Age (Hrs) | Yield[1] (g/L) | DHA (%) | FAME[2] (%) | Productivity[3] |
|---|---|---|---|---|---|
| 1 | 100.3 | 160.7 | 17.8 | 49.5 | 0.285 |
| 2 | 99.8 | 172.4 | 19.4 | 51.3 | 0.335 |
| 3 | 84.7 | 148.7 | 14.4 | 41.4 | 0.253 |
| 4 | 90.2 | 169.5 | 19.7 | 53.9 | 0.370 |
| 5 | 99.0 | 164.1 | 12.5 | 38.9 | 0.207 |
| 6 | 113.0 | 187.1 | 19.7 | 47.2 | 0.326 |
| 7 | 97.0 | 153.5 | 13.7 | 41.0 | 0.217 |
| 8 | 92.8 | 174.8 | 16.4 | 48.6 | 0.309 |
| Avg[4] | 97.1 | 166.4 | 16.7 | 46.5 | 0.288 |
| Std[5] | 8.4 | 12.3 | 2.9 | 5.4 | 0.058 |
| CV[6](%) | 8.7 | 7.4 | 17.3 | 11.7 | 20.2 |

[1]actual yield of biomass density.
[2]total fatty acid methyl esters.
[3](grams of DHA)/L/Hr.
[4]average.
[5]standard deviation.
[6]coefficients of variability. Coefficients of variability values below 5% indicates a process which has excellent reproducibility, values between 5% and 10% indicates a process which has good reproducibility and values between 10% and 20% indicates a process which has reasonable reproducibility.

Corn syrup was fed until the volume in the fermentor reached about 1,200 gallons, at which time the corn syrup addition was stopped. The fermentation process was stopped once the residual sugar concentration fell below 5 g/L. The typical age, from inoculation to final, was about 100 hours.

The fermentation broth, i.e., fermentation medium, was diluted with water using approximately a 2:1 ratio to reduce the ash content of the final product and help improve phase separation during the centrifugation step. The concentrated cell paste was heated to 160° F. (about 71° C.) and dried on a Blaw Knox double-drum dryer (42"×36"). Preferably, however, microorganisms are dried directly on a drum-dryer without prior centrifugation.

The analysis result of lipids extracted from aliquots of each entries in Table 1 is summarized in Table 2.

TABLE 2

Analysis of lipids from microorganisms of Table 1.

| Entry | % DHA relative to FAME[1] | Total Lipid % by wt. |
|---|---|---|
| 1 | 36.0 | 72.3 |
| 2 | 37.8 | 70.3 |
| 3 | 34.8 | 61.5 |
| 4 | 36.5 | 74.8 |
| 5 | 32.1 | 52.8 |
| 6 | 41.7 | 67.7 |
| 7 | 33.4 | 49.9 |
| 8 | 33.7 | 61.4 |
| Avg | 35.8 | 63.8 |
| Std.[3] | 3.0 | 9.1 |
| CV[4] (%) | 8.5 | 14.2 |

[1] see Table 1
[2] see discussion above
[3] standard deviation
[4] coefficients of variability Coefficients of variability values below 5% indicates a process which has excellent reproducibility, values between 5% and 10% indicates a process which has good reproducibility and values between 10% and 20% indicates a process which has reasonable reproducibility.

Unless otherwise stated, the fermentation medium used throughout the Examples section includes the following ingredients, where the first number indicates nominal target concentration and the number in parenthesis indicates acceptable range: sodium sulfate 12 g/L (11-13); KCl 0.5 g/L (0.45-0.55); $MgSO_4 \cdot 7H_2O$ 2 g/L (1.8-2.2); Hodag K-60 antifoam 0.35 g/L (0.3-0.4); $K_2SO_4$ 0.65 g/L (0.60-0.70); $KH_2PO_4$ 1 g/L (0.9-1.1); $(NH_4)_2SO_4$ 1 g/L (0.95-1.1); $CaCl_2 \cdot 2H_2O$ 0.17 g/L (0.15-0.19); 95 DE corn syrup (solids basis) 4.5 g/L (2-10); $MnCl_2 \cdot 4H_2O$ 3 mg/L (2.7-3.3); $ZnSO_4 \cdot 7H_2O$ 3 mg/L (2.7-3.3); $CoCl_2 \cdot 6H_2O$ 0.04 mg/L (0.035-0.045); $Na_2MoO_4 \cdot 2H_2O$ 0.04 mg/L (0-0.045); $CuSO_4 \cdot 5H_2O$ 2 mg/L (1.8-2.2); $NiSO_4 \cdot 6H_2O$ 2 mg/L (1.8-2.2); $FeSO_4 \cdot 7H_2O$ 10 mg/L (9-11); thiamine 9.5 mg/L (4-15); vitamin $B_{12}$ 0.15 mg/L (0.05-0.25) and $Ca_{1/2}$ Pantothenate 3.2 mg/L (1.3-5.1). In addition, 28% $NH_4OH$ solution is used as the nitrogen source.

The ash content of the dried microorganisms is about 6% by weight.

Example 3

This example illustrates the effect of reduced dissolved oxygen level in the fermentation medium on the productivity of microorganisms using G-tank scale.

Using the procedure described in Example 2, a 14,000 gallon nominal volume fermentation was conducted using Schizochytrium, which can be obtained using isolation processes disclosed in the above mentioned U.S. Pat. Nos. 5,340,594 and 5,340,742. The dissolved oxygen level in the fermentation medium was about 8% during the first 24 hours, about 4% from the 24$^{th}$ hour to the 40$^{th}$ hour and about 0.5% from the 40$^{th}$ hour to the end of fermentation process. Results of this lower dissolved oxygen level in fermentation medium processes are shown in Table 3.

TABLE 3

14,000 gallon scale fermentation of Schizochytrium.

| Entry | Age (Hrs) | Yield (g/L) | % DHA | % FAME | % DHA rel. to FAME | DHA Productivity (g of DHA/L/hr) |
|---|---|---|---|---|---|---|
| 1 | 82.0 | 179.3 | 21.7 | 52.4 | 41.4 | 0.474 |
| 2 | 99.0 | 183.1 | 22.3 | 55.0 | 40.5 | 0.412 |
| 3 | 72.0 | 159.3 | — | — | 40.9 | — |
| 4 | 77.0 | 161.3 | — | — | 43.2 | — |
| 5 | 100.0 | 173.0 | 23.9 | 53.3 | 44.9 | 0.413 |
| 6 | 102.0 | 183.3 | 21.6 | 50.8 | 42.6 | 0.388 |
| 7 | 104.0 | 185.1 | 23.7 | 55.0 | 43.1 | 0.422 |
| 8 | 88.0 | 179.3 | 22.3 | 52.6 | 42.4 | 0.454 |
| 9 | 100.0 | 166.4 | 22.5 | 53.5 | 42.1 | 0.374 |
| 10 | 97.0 | 182.6 | 22.8 | 51.6 | 44.1 | 0.429 |
| 11 | 87.5 | 176.5 | 19.8 | 45.6 | 43.5 | 0.399 |
| 12 | 67.0 | 170.8 | 18.8 | 48.1 | 39.1 | 0.479 |
| 13 | 97.0 | 184.9 | 23.2 | 52.7 | 44.0 | 0.442 |
| 14 | 102.0 | 181.9 | 23.6 | 52.9 | 44.6 | 0.421 |
| 15 | 102.0 | 186.9 | 19.9 | 47.8 | 41.8 | 0.365 |
| 16 | 97.0 | 184.4 | 19.6 | 45.5 | 43.0 | 0.373 |
| 17 | 98.0 | 174.7 | 19.7 | 45.1 | 43.7 | 0.351 |
| 18 | 103.5 | 178.8 | 18.3 | 44.5 | 41.2 | 0.316 |
| 19 | 102.0 | 173.7 | 15.8 | 43.1 | 36.7 | 0.269 |
| 20 | 94.0 | 190.4 | 19.3 | 46.9 | 41.1 | 0.391 |
| 21 | 72.0 | 172.5 | 22.8 | 52.8 | 43.2 | 0.546 |
| 22 | 75.0 | 173.1 | 21.0 | 51.7 | 40.8 | 0.485 |
| 23 | 75.0 | 152.7 | 20.3 | 50.3 | 40.4 | 0.413 |
| 24 | 75.5 | 172.5 | 21.9 | 51.7 | 42.3 | 0.500 |
| 25 | 61.0 | 156.4 | 17.3 | 45.7 | 37.8 | 0.444 |
| 26 | 74.5 | 150.6 | 20.2 | 50.1 | 40.2 | 0.408 |
| 27 | 70.5 | 134.3 | 14.8 | 40.6 | 36.6 | 0.282 |
| 28 | 75.5 | 146.1 | 21.3 | 49.7 | 42.8 | 0.412 |
| 29 | 82.0 | 174.3 | 21.4 | 50.4 | 42.5 | 0.455 |
| 30 | 105.0 | 182.3 | 21.7 | 50.7 | 42.8 | 0.377 |
| 31 | 66.0 | 146.2 | 16.4 | 44.6 | 36.7 | 0.363 |
| Avg | 87.2 | 171.5 | 20.6 | 49.5 | 41.6 | 0.409 |
| Std | 13.9 | 14.1 | 2.4 | 3.8 | 2.3 | 0.061 |
| CV | 16.0% | 8.2% | 11.6% | 7.7% | 5.5% | 15.0% |

Example 4

This example illustrates the effect of reduced dissolved oxygen level in the fermentation medium on the productivity of microorganisms on a 41,000 gallon scale.

Same procedure as Example 3 in a 41,000 gallon fermentor was performed. Results are shown in Table 4.

TABLE 4

41,000 gallon scale fermentation of Schizochytrium

| Entry | Age (Hrs) | Yield (g/L) | % DHA | % FAME | % DHA rel. to FAME | DHA Productivity (g of DHA/L/hr) |
|---|---|---|---|---|---|---|
| 1 | 75.0 | 116.1 | 17.3 | 46.1 | 37.4 | 0.268 |
| 2 | 99.0 | 159.3 | 17.4 | 47.0 | 37.1 | 0.280 |
| 3 | 103.0 | 152.6 | 16.0 | 47.2 | 33.8 | 0.237 |
| 4 | 68.0 | 136.8 | 17.9 | 45.9 | 39.1 | 0.360 |
| 5 | 84.0 | 142.0 | 17.5 | 47.0 | 37.2 | 0.296 |
| Avg | 85.8 | 141.4 | 17.2 | 46.6 | 36.9 | 0.288 |
| Std | 15.1 | 16.6 | 0.7 | 0.6 | 1.9 | 0.046 |
| CV | 17.5% | 11.8 | 4.2% | 1.3% | 5.2% | 15.8% |

Example 5

This example illustrates the affect of extra nitrogen on the fermentation process of the present invention.

Four sets of 250-L scale fed-batch experiments were conducted using a procedure similar to Example 3. Two control experiments and two experiments containing extra ammonia (1.15× and 1.25× the normal amount) were conducted. Results are shown in Table 5.

TABLE 5

Affects of extra ammonia on fermentation of *Schizochytrium*.

| Age (hrs) | Yield (g/L) | Biomass Productivity | Conversion Efficiency | DHA Content | FAME Content | DHA Productivity |
|---|---|---|---|---|---|---|
| Sugar target: 7 g/L, Base pH set point: 5.5, Acid pH set point: 7.3, 1.0× $NH_3$ | | | | | | |
| 48 | 178 | 3.71 g/L/hr | 51.5% | 10.7% | 37.8% | 0.40 g/L/hr |
| 60 | 185 | 3.08 g/L/hr | 46.9% | 16.3% | 47.2% | 0.50 g/L/hr |
| 72 | 205 | 2.85 g/L/hr | 45.2% | 17.4% | 47.4% | 0.50 g/L/hr |
| 84 | 219 | 2.61 g/L/hr | 43.8% | 17.1% | 45.5% | 0.45 g/L/hr |
| 90 | 221 | 2.46 g/L/hr | 44.1% | 18.4% | 48.9% | 0.45 g/L/hr |
| Sugar target: 7 g/L, Base pH set point: 5.5, Acid pH set point: 7.3, 1.15× $NH_3$ | | | | | | |
| 48 | 171 | 3.56 g/L/hr | 55.6% | 12.0% | 36.3% | 0.43 g/L/hr |
| 60 | 197 | 3.28 g/L/hr | 54.6% | 9.4% | 38.4% | 0.31 g/L/hr |
| 72 | 191 | 2.65 g/L/hr | 52.8% | 9.4% | 40.0% | 0.25 g/L/hr |
| 84 | 190 | 2.26 g/L/hr | 52.5% | 10.0% | 42.5% | 0.23 g/L/hr |
| 90 | 189 | 2.10 g/L/hr | 52.2% | 9.2% | 43.3% | 0.19 g/L/hr |
| Sugar target: 7 g/L, Base pH set point: 5.5, Acid pH set point: 7.3, 1.25× $NH_3$ | | | | | | |
| 48 | 178 | 3.71 g/L/hr | 56.4% | 11.5% | 33.7% | 0.43 g/L/hr |
| 60 | 179 | 2.98 g/L/hr | 48.6% | 10.3% | 36.0% | 0.31 g/L/hr |
| 72 | 180 | 2.50 g/L/hr | 48.8% | 12.0% | 37.6% | 0.30 g/L/hr |
| 84 | 181 | 2.15 g/L/hr | 46.1% | 13.6% | 40.1% | 0.29 g/L/hr |
| 90 | 185 | 2.06 g/L/hr | 45.7% | 12.6% | 40.7% | 0.26 g/L/hr |
| Sugar target: 7 g/L, Base pH set point: 5.5, Acid pH set point: 7.3, 1.0× $NH_3$ | | | | | | |
| 48 | 158 | 3.29 g/L/hr | 55.7% | 13.1% | 36.5% | 0.43 g/L/hr |
| 60 | 174 | 2.90 g/L/hr | 48.9% | 17.9% | 39.2% | 0.52 g/L/hr |
| 72 | 189 | 2.63 g/L/hr | 45.7% | 21.0% | 39.4% | 0.55 g/L/hr |
| 84 | 196 | 2.33 g/L/hr | 44.1% | 22.4 | 40.1% | 0.52 g/L/hr |
| 90 | 206 | 2.29 g/L/hr | 44.8% | 22.1% | 40.3% | 0.51 g/L/hr |

In general, extra nitrogen has a negative effect on fermentation performance, as significant reductions were observed in the DHA productivity for the two batches where extra ammonia were added. As shown on Table 5, the control batches resulted in final DHA levels of 18.4% and 22.1% versus the 9.2% (1.15× ammonia) and 12.6% (1.25× ammonia) for extra nitrogen supplemented batches.

Example 6

This example shows a kinetic profile of a fermentation process of the present invention.

A 1000 gallon scale fed-batch experiment was conducted using a procedure similar to Example 3. Kinetic profile of the fermentation process is shown in Table 6.

TABLE 6

Kinetic Profile for a 1,000 gallon scale Fed-Batch fermentation of *Schizochytrium*.

| Age (hrs) | Yield (g/L) | Biomass Productivity | Conversion Efficiency | % DHA Content | % FAME Content | DHA Productivity |
|---|---|---|---|---|---|---|
| 24 | 118 | 4.92 g/L/hr | 78.2% | 7.4 | 18.8 | 0.36 g/L/hr |
| 30 | 138 | 4.60 g/L/hr | 60.3% | 10.6 | 30.9 | 0.49 g/L/hr |
| 36 | 138 | 3.83 g/L/hr | 46.6% | 11.6 | 36.5 | 0.44 g/L/hr |
| 42 | 175 | 4.17 g/L/hr | 49.8% | 13.4 | 41.7 | 0.56 g/L/hr |
| 48 | 178 | 3.71 g/L/hr | 45.1% | 18.7 | 52.8 | 0.69 g/L/hr |
| 48* | 164 | 3.42 g/L/hr | 41.5% | 15.3 | 33.1 | 0.52 g/L/hr |
| 54 | 196 | 3.63 g/L/hr | 45.7% | 16.6 | 51.2 | 0.60 g/L/hr |
| 60 | 190 | 3.17 g/L/hr | 41.7% | 16.9 | 33.9 | 0.54 g/L/hr |
| 72 | 189 | 2.62 g/L/hr | 39.1% | 15.6 | 31.8 | 0.41 g/L/hr |
| 84 | 195 | 2.32 g/L/hr | 38.5% | 16.4 | 32.7 | 0.38 g/L/hr |
| 90 | 200 | 2.22 g/L/hr | 39.0% | 18.8 | 33.3 | 0.42 g/L/hr |
| 90 | 171 | 1.90 g/L/hr | 33.3% | 22.2 | 61.6 | 0.42 g/L/hr** |

*Two separate samples were analyzed at 48 hrs.
**This is for a washed dry-cell weights (DCW) sample. Other reported values are for unwashed samples.

Example 7

This example illustrates affect of the amount of carbon source on productivity.

Three different fermentation processed using the process of Example 3 were conducted using various amounts of carbon source. Results are shown on Table 7.

TABLE 7

Fermentation results for various amounts of carbon source on fermentation of *Schizochytrium*.

| Age (hrs) | Yield (g/L) | Carbon Charge | Conversion Efficiency | % DHA Content | % FAME Content | Productivity (g/L/hr) |
|---|---|---|---|---|---|---|
| 90 | 171 | 51.3% | 33.3% | 22.2 | 61.6 | 0.42 |
| 94 | 122 | 40.5% | 30.1% | 19.1 | 57.3 | 0.25 |
| 59 | 73 | 20.0% | 36.5% | 11.9 | 40.8 | 0.15 |

The present invention, in various embodiments, includes components, methods, processes, systems and/or apparatus substantially as depicted and described herein, including various embodiments, subcombinations, and subsets thereof. Those of skill in the art will understand how to make and use the present invention after understanding the present disclosure. The present invention, in various embodiments, includes providing devices and processes in the absence of items not depicted and/or described herein or in various embodiments hereof, including in the absence of such items as may have been used in previous devices or processes, e.g., for improving performance, achieving ease and\or reducing cost of implementation.

The foregoing discussion of the invention has been presented for purposes of illustration and description. The foregoing is not intended to limit the invention to the form or forms disclosed herein. Although the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/ or equivalent structures, functions, ranges or steps are disclosed herein, and without intending to publicly dedicate any patentable subject matter.

What is claimed is:

1. A process for growing microorganisms of the order Thraustochytriales by conducting a fermentation of the microorganisms in a fermentation medium comprising a carbon source and a limiting nutrient source, the process comprising:
   a) providing the fermentation medium comprising the carbon source and limiting nutrient source;
   b) adding the microorganisms to the fermentation medium;
   c) adding an additional amount of the carbon source and limiting nutrient source to the fermentation medium to increase the biomass density of the fermentation medium when the dissolved oxygen content of the fermentation medium is at least 4% of saturation;
   d) adding an additional amount of the carbon source while limiting the amount of limiting nutrient source added to the fermentation medium and allowing the dissolved oxygen content of the fermentation medium to decrease to less than about 3% of saturation;
   wherein lipid production is induced in the microorganisms; and
   e) recovering at least some of the lipids from the microorganisms;
   wherein the process produces at least an average rate of 0.5 grams lipids per liter of fermentation medium per hour fermentation
   wherein at least about 15% of the total lipids produced by the microorganisms is polyunsaturated fatty acids, and
   wherein the lipids are at least 20% by weight of the dry cell weight of the biomass.

2. The process of claim 1, wherein the process is a fed batch process.

3. The process of claim 1, wherein the microorganisms produce lipids containing polyunsaturated fatty acids when the dissolved oxygen content of the fermentation medium is less than 1% of saturation.

4. The process of claim 1, wherein the microorganisms are selected from the group consisting of *Thraustochytrium, Schizochytrium*, and mixtures thereof.

5. The process of claim 1, wherein the process produces on average at least 0.2 grams docosahexaenoic acid per liter of fermentation medium per hour fermentation.

6. The process of claim 1, wherein the microorganisms are *Schizochytrium*.

* * * * *